United States Patent
Hirsch

(10) Patent No.: US 10,966,881 B1
(45) Date of Patent: Apr. 6, 2021

(54) ABSORBENT GARMENT INSERT

(71) Applicant: Gary F Hirsch, Redwood City, CA (US)

(72) Inventor: Gary F Hirsch, Redwood City, CA (US)

( * ) Notice: Subject to any disclaimer, the term of this patent is extended or adjusted under 35 U.S.C. 154(b) by 0 days.

(21) Appl. No.: 16/578,028

(22) Filed: Sep. 20, 2019

Related U.S. Application Data

(60) Provisional application No. 62/734,778, filed on Sep. 21, 2018.

(51) Int. Cl.
| | |
|---|---|
| *A61F 13/15* | (2006.01) |
| *A61F 13/512* | (2006.01) |
| *A61F 13/56* | (2006.01) |
| *A61F 13/49* | (2006.01) |
| *A61F 13/514* | (2006.01) |
| *A61F 13/515* | (2006.01) |

(52) U.S. Cl.
CPC ...... *A61F 13/512* (2013.01); *A61F 13/49058* (2013.01); *A61F 13/515* (2013.01); *A61F 13/51401* (2013.01); *A61F 13/5611* (2013.01); *A61F 2013/51407* (2013.01); *A61F 2013/51425* (2013.01)

(58) Field of Classification Search
CPC .............. A61F 13/512; A61F 13/49058; A61F 13/51401; A61F 13/515; A61F 13/5611; A61F 2013/51407; A61F 2013/51425
USPC ............. 604/378, 379, 380, 381, 383, 385.3
See application file for complete search history.

(56) References Cited

U.S. PATENT DOCUMENTS

| | | | | |
|---|---|---|---|---|
| 3,886,941 A | * | 6/1975 | Duane | A61F 13/51305 604/370 |
| 5,156,902 A | * | 10/1992 | Pieper | A61F 13/15577 428/206 |
| 5,304,161 A | | 4/1994 | Noel et al. | |
| 5,545,464 A | | 8/1996 | Stokes | |
| 5,552,012 A | | 9/1996 | Morris et al. | |
| 5,562,646 A | | 10/1996 | Goldman et al. | |
| 5,731,061 A | * | 3/1998 | Bezier | A61F 13/15731 264/504 |
| 6,068,620 A | | 5/2000 | Chmielewski | |
| 6,570,059 B1 | * | 5/2003 | Carlucci | A61F 13/5146 604/367 |
| 6,627,791 B1 | * | 9/2003 | Veglio | A61F 13/5146 428/132 |
| 6,972,011 B2 | | 12/2005 | Made et al. | |
| 7,232,300 B2 | | 6/2007 | Walter | |
| 7,772,450 B2 | | 8/2010 | Zhang et al. | |
| 8,206,533 B2 | | 6/2012 | Hundorf et al. | |
| 8,425,729 B2 | | 4/2013 | Skoog et al. | |
| 9,065,033 B2 | | 6/2015 | Fenske | |
| 9,295,593 B2 | | 3/2016 | Van Malderen | |
| 9,549,858 B2 | | 1/2017 | Yang | |

(Continued)

FOREIGN PATENT DOCUMENTS

| | | |
|---|---|---|
| EP | 3153141 A1 | 9/2016 |
| WO | 2013153235 A1 | 10/2015 |

*Primary Examiner* — Jacqueline F Stephens
(74) *Attorney, Agent, or Firm* — Edward S. Sherman

(57) ABSTRACT

An absorbent member is intended for insertion in diapers to boost the absorptive capacity. The construction increases the flow of fluid to the diaper, yet in preferred embodiments, blocks the reflow of fluid pressed of the diaper from reaching the wearer to reduce the propensity to cause or aggravate diaper rash.

12 Claims, 15 Drawing Sheets

(56) References Cited

U.S. PATENT DOCUMENTS

| | | | |
|---|---|---|---|
| 2002/0143316 A1* | 10/2002 | Sherrod | A61F 13/505 |
| | | | 604/385.101 |
| 2003/0129915 A1 | 7/2003 | Harris | |
| 2003/0163105 A1* | 8/2003 | Tears | A61F 13/4752 |
| | | | 604/378 |
| 2015/0065974 A1 | 3/2015 | Michael et al. | |
| 2015/0164710 A1 | 6/2015 | Ehkme | |
| 2016/0175169 A1 | 6/2016 | Bianchi et al. | |
| 2017/0258650 A1 | 9/2017 | Rosatti | |

* cited by examiner

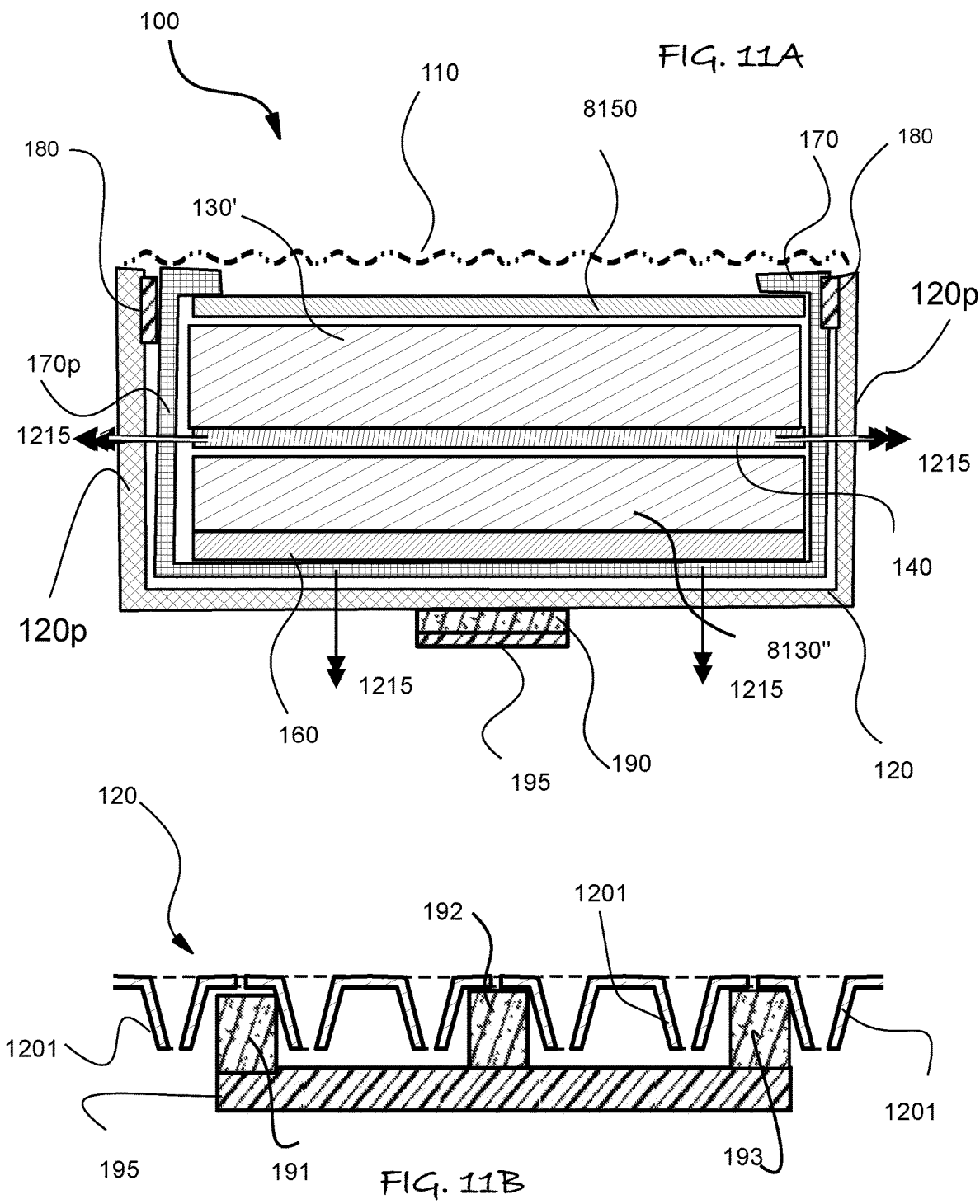

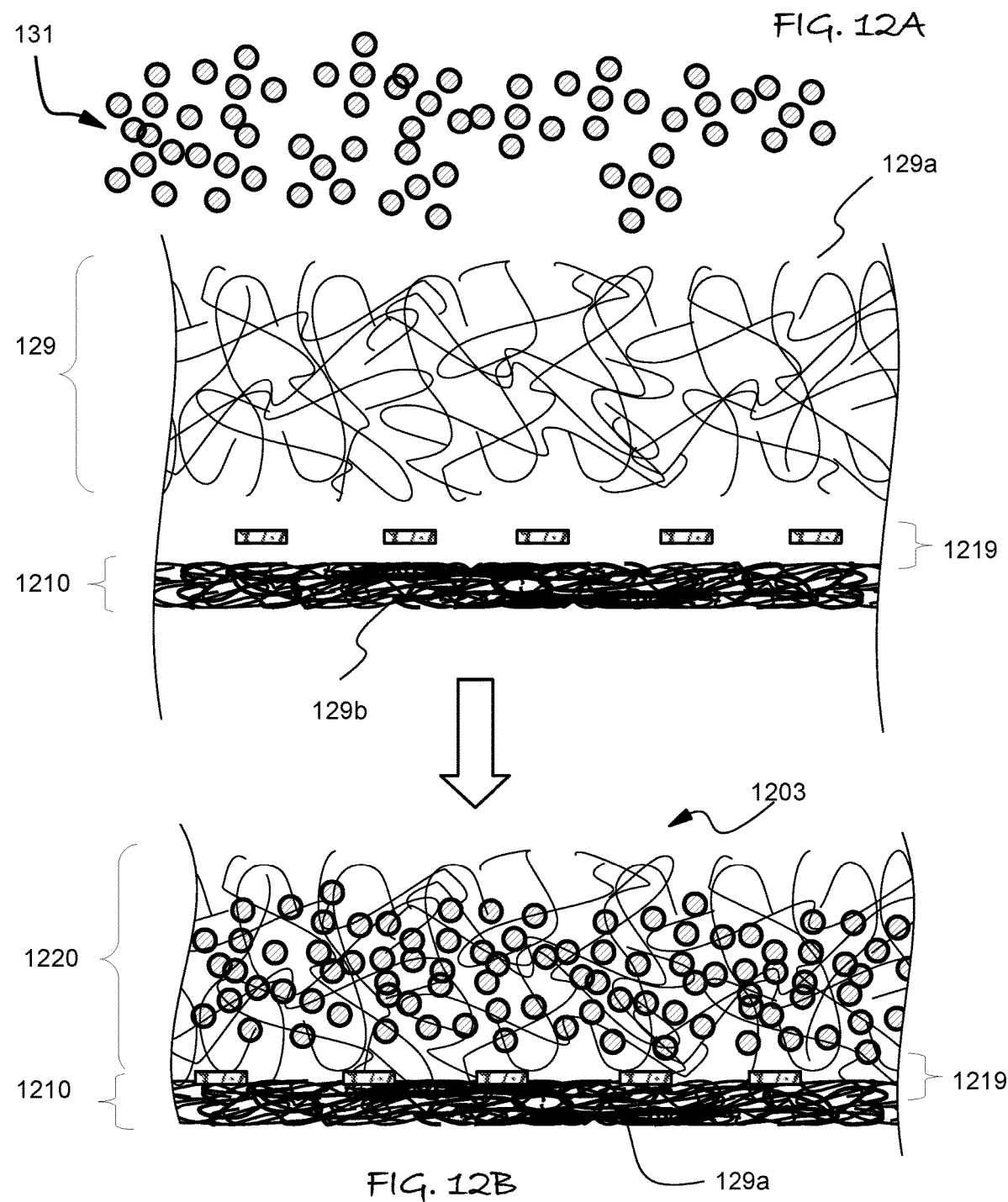

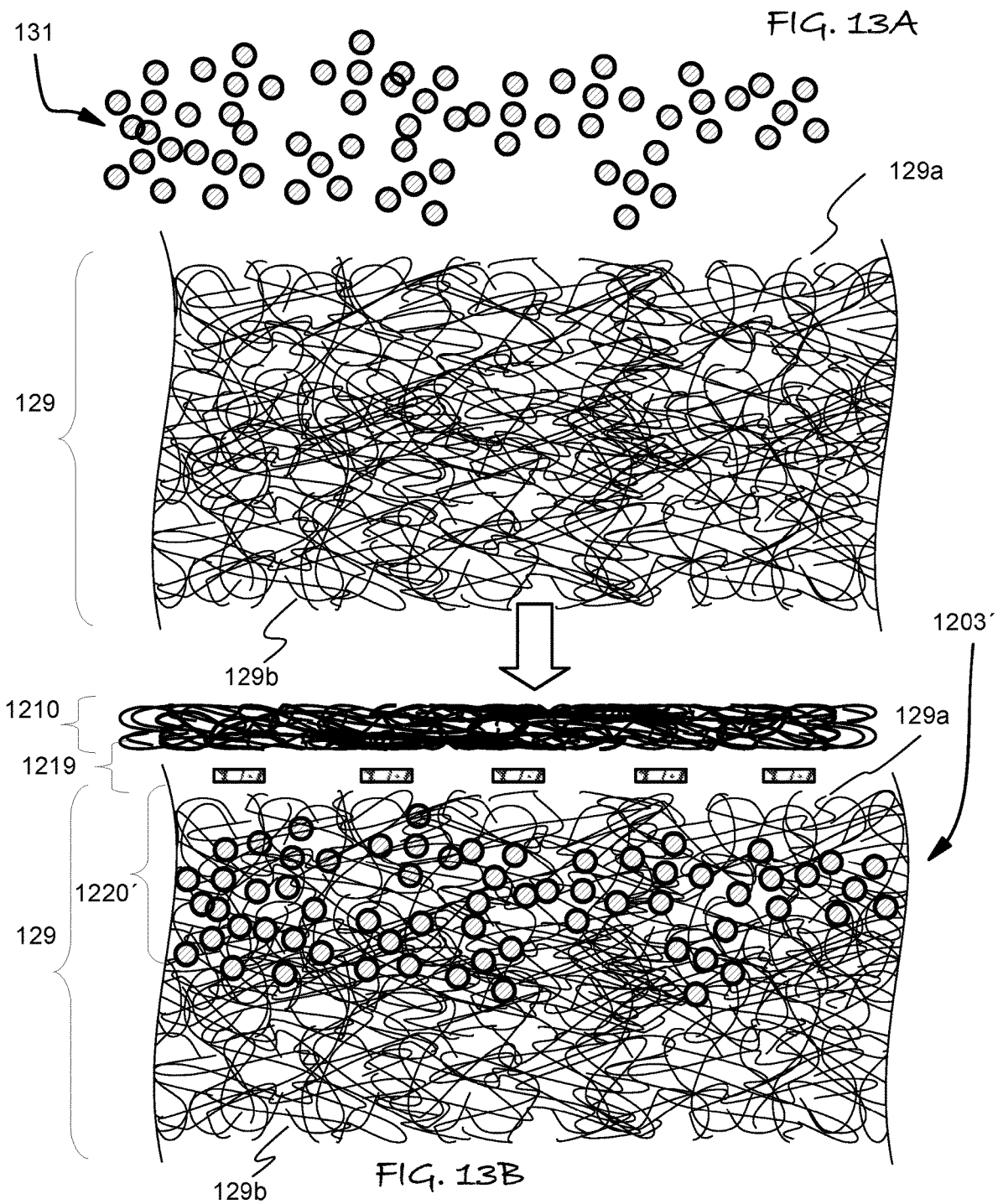

ABSORBENT GARMENT INSERT

CROSS-REFERENCE TO RELATED APPLICATIONS

The present application claims the benefit of priority to the U.S. provisional patent application of the same title that was filed on Sep. 21, 2018 and has application Ser. No. 62/734,778, which is incorporated herein by reference.

BACKGROUND OF INVENTION

The field of inventions is diapers and incontinence garments.

Diapers have a limited fluid holding capacity before they have to be changed.

For some individuals, this capacity may not be sufficient to allow a caregiver to sleep for eight hours without having to change the diaper.

Further, it is unhealthy to expose skin to dampness for too long, as it can cause diaper rash and fungal infections. In the case of adults, it can leads to skin ulcers from urine attack on the skin and at contributing to the formation of dicubitous ulcers (bed sores) from pressure point.

The absorbent capacity of ordinary diapers can be increased by inserting what is known as a booster or booster pad, which generally contains the same fluid absorbent fillers as ordinary diapers, but is covered with a porous fabric such as a non woven fabric. The booster generally has a somewhat rectangle shape, being configured for placement in the diaper so that is it passes between the legs of the wearer, extending upward to just below the waist.

While boosters can increase a diaper's capacity somewhat, and may better enable eight hours for some individuals, this can still expose the wearer's skin to excess bodily fluids for far too long. Further, such booster while adding some absorptive capacity may also diminish the available capacity of the diaper it is inserted into. This is because the urine must flow into the booster before it can reach the main absorptive component of the diaper. As the booster initially absorbs the initial discharge of urine, it may prevent it and further urine discharges from flowing into the other parts of the diaper. When the urine finally reaches the absorptive material within the diaper, the convention booster pad may be rather soggy and exposes the skin of the user to their bodily fluids.

In light of the aforementioned deficiencies of booster pads, when used in combination with diapers, briefs, protective underwear or belted shields the following are various objectives of the invention.

A first objective of the invention is to improve the efficiency of the absorbent material in diapers and related incontinence garments.

Another objective of the invention is to boost the urine and fluid absorptive capacity, without excessively increasing the weight and bulk.

Another objective of the invention is to improve the comfort of the user that is wearing such garments.

Another objective of the invention is to prevent diaper rash.

Another objective is to prevent diaper rash and related skin ulcers when the combination of a diaper or related incontinence garment is worn with a booster inserted therein for at least about 6-8 hours.

The above and other objects, effects, features, and advantages of the present invention will become more apparent from the following description of the embodiments thereof taken in conjunction with the accompanying drawings

SUMMARY OF INVENTION

In the present invention, the first object is achieved by providing a generally planar absorbent member comprising an upper cover, a lower cover opposing the upper cover, at least a layer of an absorbent filling material comprising super absorbent polymer (SAP) particles disposed in a network including at least one of fibers, non-woven fibers, and structured layer of fibers, wherein the upper cover and lower cover are sealed about a common perimeter to contain the absorbent filling material in an interior cavity, and the upper cover comprising a porous fabric and the lower cover comprising a flexible film adapted to transmit fluid or urine flow from the interior cavity and block fluid or urine flow into the interior cavity.

A second aspect of the invention is characterized by such a generally planar absorbent member wherein the upper cover is a 3D non woven fabric.

Another aspect of the invention is characterized by any such generally planar absorbent member wherein the lower cover is an apertured film comprising an array perforations, each perforation of the array having a perimeter surrounded by a base of a frustoconical shaped protrusion that extend away from the lower cover to an open apex.

Another aspect of the invention is characterized by any such generally planar absorbent member having a generally rectangular shape with an aspect ratio of between about 5 to about 30 and a width of greater than 1 inch about and less than about 6 inches.

Another aspect of the invention is characterized by any such generally planar absorbent member wherein the lower cover has an exterior surface facing away from the upper cover, the exterior surface being adapted to be adhered on one or more portions thereof to a fabric member.

Another aspect of the invention is characterized by any such generally planar absorbent member wherein the lower cover has an exterior surface facing away from the upper cover and further comprising one or more regions of pressure surface adhesive on the exterior surface of the lower cover.

Another aspect of the invention is characterized by any such generally planar absorbent member wherein the one or more regions of pressure sensitive adhesive are adjacent stripes.

Another aspect of the invention is characterized by any such generally planar absorbent member in which the pressure adhesive coated region on the exterior surface of the lower cover are covered with a removable release film.

Another aspect of the invention is characterized by a generally planar absorbent member comprising an upper cover, a lower cover opposing the upper cover, a plurality of layers of an absorbent filling material consisting essentially of super absorbent polymer (SAP) particles dispersed in a network of non-hydrophilic fibers, wherein the upper cover and lower cover are sealed about a common perimeter to contain the absorbent filling material in an interior cavity, and the upper cover and the lower cover comprising a porous fabric, wherein each of the layers in the plurality are adapted to have a different rate at which the SAP particles will swell when absorbing fluid.

Another aspect of the invention is characterized by any such generally planar absorbent member wherein at least one of the layers in the plurality has a mixture of different SAP particles, in which some of the SAP particles have a different rate of fluid absorption that the other SAP particles in the mixture.

Another aspect of the invention is characterized by any such generally planar absorbent member wherein the upper cover is a 3D non woven fabric.

Another aspect of the invention is characterized by any such generally planar absorbent member wherein the lower cover is an apertured film comprising an array perforations, each perforation of the array having a perimeter surrounded by a base of a frustoconical shaped protrusion extend away from the lower cover to an open apex.

Another aspect of the invention is characterized by any such generally planar absorbent member having a generally rectangular shape with an aspect ratio of between about 5 to about 30 and a width of greater than 1 inch about and less than about 6 inch.

Another aspect of the invention is characterized by any such generally planar absorbent member wherein the lower cover has an exterior surface facing away from the upper cover, the exterior surface being adapted to be adhered on one or more portions thereof to a fabric member.

Another aspect of the invention is characterized by any such generally planar absorbent member wherein the lower cover has an exterior surface facing away from the upper cover and further comprising one or more regions of pressure sensitive adhesive on the exterior surface of the lower cover.

Another aspect of the invention is characterized by any such generally planar absorbent member wherein the one or more regions of pressure sensitive adhesive are adjacent stripes.

Another aspect of the invention is characterized by any such generally planar absorbent member in which the pressure sensitive adhesive coated region on the exterior surface of the lower cover are covered with a removable release film.

Another aspect of the invention is characterized by a generally planar absorbent member comprising an upper cover, a lower cover opposing the upper cover, a plurality of layers of an absorbent filling material consisting essentially of super absorbent polymer (SAP) particles dispersed in a network of non-hydrophilic fibers, wherein the upper cover and lower cover are sealed about a common perimeter to contain the absorbent filling material in an interior cavity, and the upper cover and the lower cover comprising a porous fabric, wherein the network of non-hydrophilic fibers expands as the SAP particles swell when absorbing fluid, wherein at least some of the SAP particles is extruded out of the network as the absorbing filling material reaches a total absorbent capacity.

Another aspect of the invention is characterized by any such generally planar absorbent member in which the upper cover comprises a porous fabric and the lower cover comprising a flexible film adapted to transmit fluid or urine flow from the interior cavity and block fluid or urine flow into the interior cavity.

Another aspect of the invention is characterized by any such generally planar absorbent member wherein the lower cover has an exterior surface facing away from the upper cover, the exterior surface being having one or more portion with an adhesive material for attachment to non-woven fabric of a diaper.

The above and other objects, effects, features, and advantages of the present invention will become more apparent from the following description of the embodiments thereof taken in conjunction with the accompanying drawings.

BRIEF DESCRIPTION OF DRAWINGS

FIGS. 2A and 2B respectively illustrate an embodiment of the absorbent garment insert in orthogonal elevation views, whereas FIG. 2C is a schematic enlarged cross-sectional elevation from region C in FIG. 2A, and FIG. 2D is an enlarged portion of FIG. 2C.

FIGS. 3A and B respectively illustrate a more preferred embodiment of the absorbent garment insert in orthogonal elevation views, whereas FIG. 3C is a schematic enlarged cross-sectional elevation from region C in FIG. 3A FIGS. 4A and 4B schematically illustrate inventive principles in using the embodiment in FIG. 3A-3C as a booster pad.

FIG. 11A is a schematic cross-sectional elevation according to the orientation in FIG. 2B, to illustrate additional aspects of the invention. FIG. 11B is an expanded cross-sectional elevation view of a portion of FIG. 11A illustrating an alternative embodiment.

FIGS. 12A and 12B are schematic diagrams illustrating steps in a method of forming the absorbent core of the various embodiments.

FIGS. 13A and 13B are schematic diagrams illustrating alternative steps in a method of forming the absorbent core of the various embodiments.

DETAILED DESCRIPTION

Figure 1:
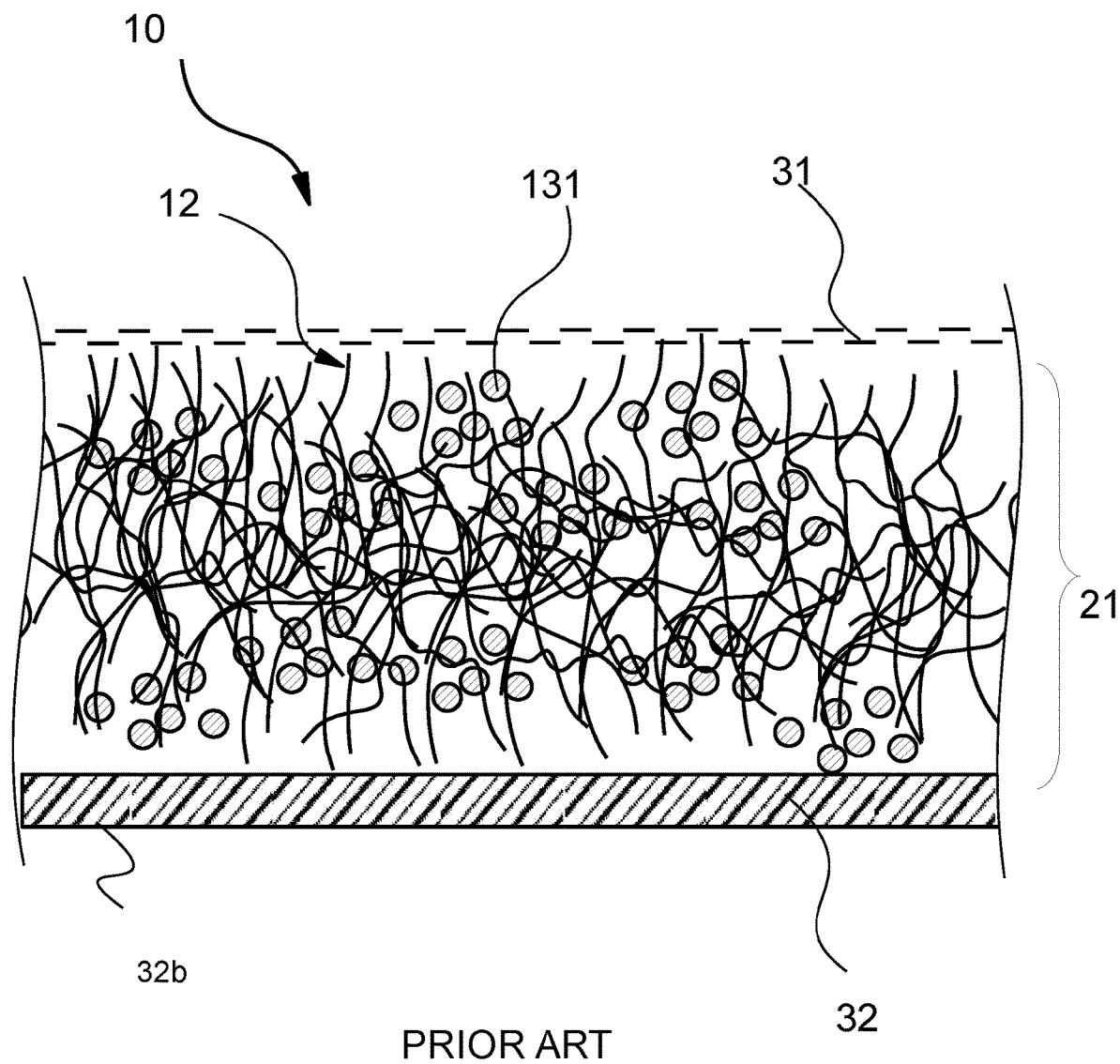
FIG. 1 is a cross-sectional elevation view of the layers of materials used in absorbent pads or sheets used to form conventional diapers and related wearable garments.
Figure 2:
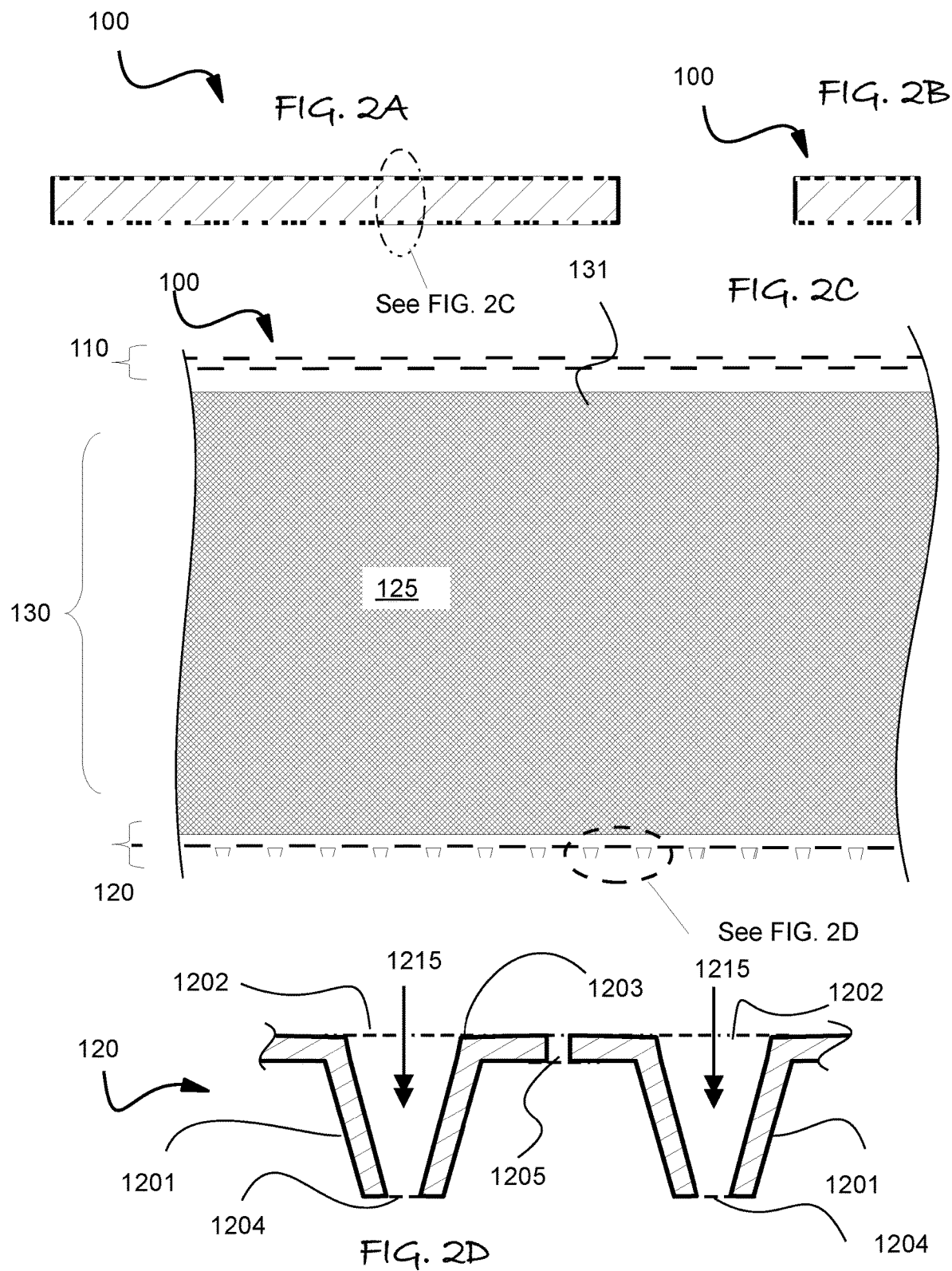
Figure 3:
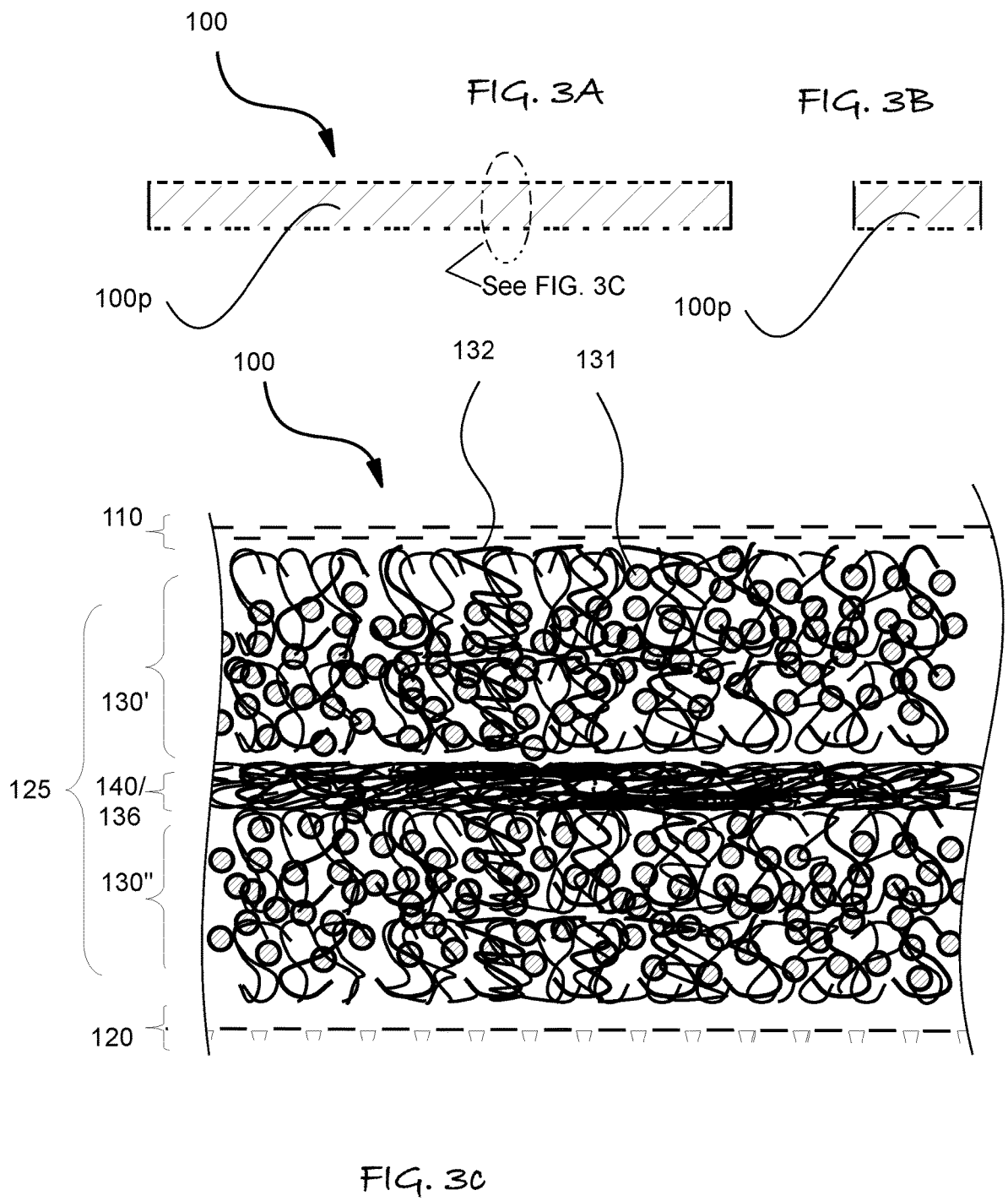
Figure 4:
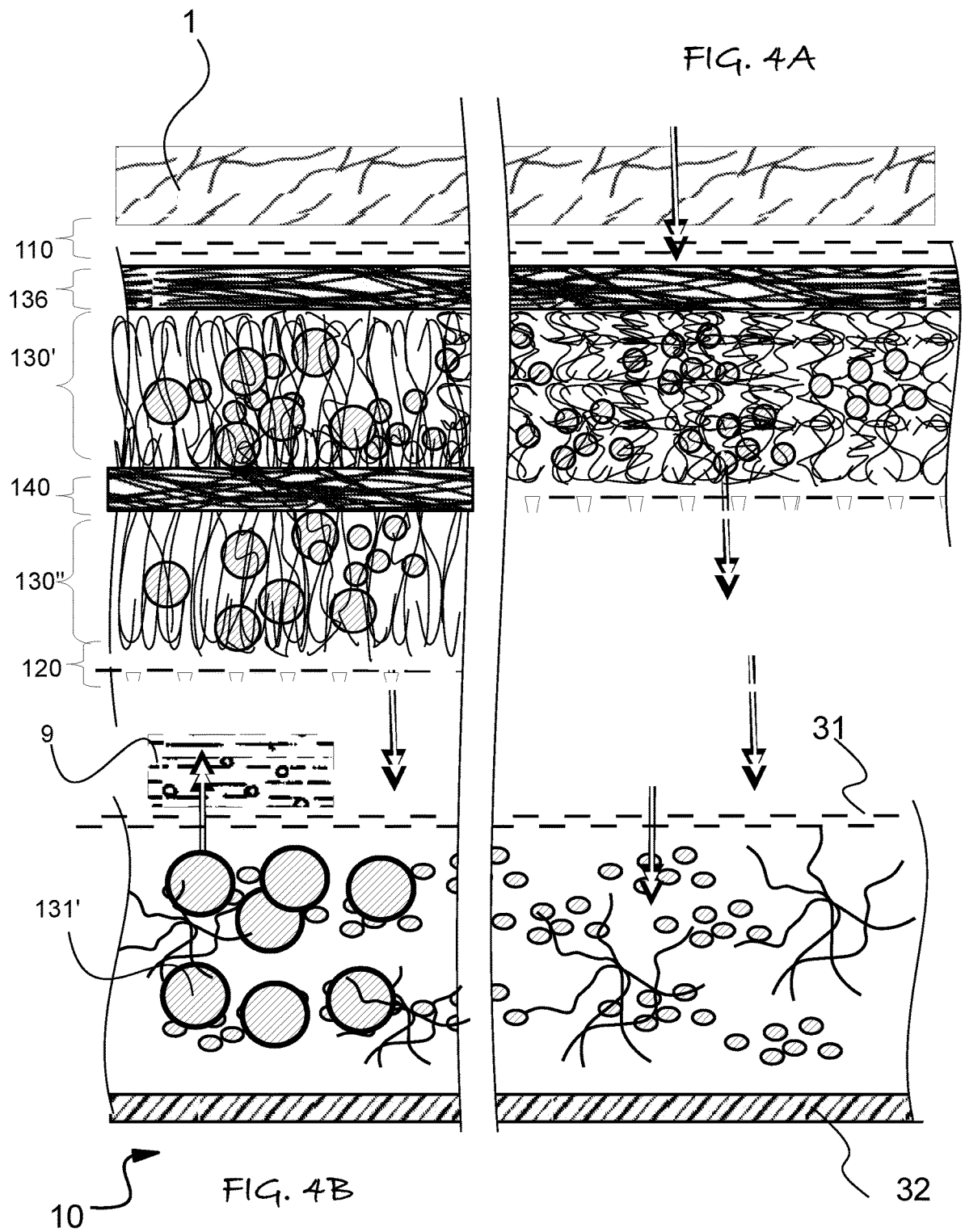

Referring to FIGS. 1 through 15, wherein like reference numerals refer to like components in the various views, there is illustrated therein a new and improved absorbent garment insert, generally denominated 100 herein.

Absorbent garment inserts 100 can be used to form or within absorbent garments, such as diapers, wound dressings, sanitary pads, and leakage pads for wearing under conventional undergarments. Hence, by diaper we mean a body-worn member having some absorptive capacity of any type of bodily discharge, such as urine, feces, blood and the like. Accordingly, the term diaper or diapers is intended to embrace what is also referred to as diapers, briefs, protective underwear or belted shields and the like, which may be intended for use by adults, children, toddlers, and infants. Absorbent garment inserts can also be used to supplement the capacity of any type of absorbent garment. In the case of adult or baby diapers, which have an fluid or urine absorbent core facing the skin, such an additional absorbent garment insert is known as a booster pad, as it is intended to supplement the capacity of the absorbent core of a form-fitting diaper or pull up style protective garment, allowing the wearer to go longer without having to change the diaper or garment. In the case of using booster pads in baby or infant diapers, while a normal diaper might last 3-5 hours of day time use until it becomes fluid or urine saturated and needs to be changed to prevent skin rash, the booster is intended to extend the life by several more hours, so that parents can sleep through the night or at least about 6 hours before having to get up and change the diaper.

It should be appreciated that conventional diaper garments 10, such as illustrated in FIG. 1, generally contain a mixture of super absorbent polymer (SAP) particles 131 and fiber fluff 12 in a core 21, with a waterproof outer plastic layer 32, and a porous upper layer 31. The porous upper layer 31 faces the wearer. Considerable progress has been made in improving diapers to use more SAP particles 131 and less fiber fluff 12 or other fillers. The reduction of fiber fluff 12 reduces the weight and bulk of diapers. Since fiber fluff 12 is generally hydrophilic, it is wetted by water and other fluids, including urine, which is then loosely bound by surface tension as a fluid outer layer. Hence, when pressure is applied any excess fluid or urine that is not strongly bound in the swollen SAP particles is readily released and can ooze out through the porous upper layer 31 to contact the skin of the wearer. The SAP particles 131 however, can form stable fluid/urine swollen gels that retain such body fluids under pressure. However, the SAP particles 131 needs to be dispersed and supported within a matrix and/or between additional layers so that it is more effective in absorbing fluid or urine without creating solid gel-like dams that block the flow of additional fluid or urine to dry gel. This phenomenon is known as gel-blocking.

In any laminated construction of absorbent materials, such gel-blocking can occur when the SAP particles of absorbent polymer material located in the layer or regions of first contact with fluid or urine start to increase in volume as a consequence of imbibing the fluid or urine, thereby forming a hydrogel. When absorbent polymer material concentrations are high, relative to another component that provides liquid wicking or channel for liquid flow, and expand as they become more saturated with fluid or urine, they each form an in individual swollen hydro-gel, which can essentially merge into a continuous gel-like mass, and block initial and/or additional fluid or urine from reaching other more absorbent regions of the absorbent core, thus leading to unappreciated, underused and/or unused absorbent capacity.

Accordingly, when a diaper deploys relatively little fiber fluff, it may include additional layers to laterally distribute fluid or urine before it reaches the dry SAP particles, and the resulting swollen SAP particles being a gel, is desirably held or immobilized in a manner that provides or creates channel for additional fluid or urine to reach SAP particles that have remained dry. These additional layers have come to be referred by the acronyms "ADL" for Acquisition and Distribution Layer, as well as "ADC" for acquisition distribution and containment layers, and are disclosed in U.S. Pat. No. 5,304,161, which is incorporated herein by reference. Such an ADL or ADC is generally a thin porous member or membrane that laterally distributes fluid or urine as it passes; it may have random channels that force the fluid or urine to diffuse laterally as it flows downward due to gravity. This prevents immediate gel block in the small lateral region of a containment layer that comprises a significant amount of SAP particles, but does not preclude gel blocking in deeper layers or locally as the SAP particles approach full saturation with fluid or urine.

The inventive diaper booster pad or absorbent garment insert 100 can be successfully deployed with thin diapers containing little fiber fluff, as well as conventional diapers in which the total absorptive capacity of the fiber fluff is much greater than the SAP particles. By deploying, we mean the booster pad or absorbent garment insert 100 is inserted in the diaper above the porous upper layer 31, proximal to the wearer's skin to extend between the legs of the wear to generally cover the genitals, perineum and anal regions to directly receive urine, feces and/or menstrual discharges.

It should first be appreciated that the inventor has come to recognize what those of ordinary skill in the art of absorptive garments, such as a diaper, pull-ups and the like, have failed to appreciate; when booster pads are used, the wearer tends to be wearing them for an extended period of time. During such extended period of time, while the diaper may not have reached its absorptive capacity, the portion of the diaper and the booster most proximal to the wearer's skin are likely to be totally swollen with urine. Under such conditions, the skin will be exposed to moisture longer, and the diaper's absorptive core material may no longer have capacity to wick the fluid or urine away from the skin. Moreover, as booster pads are used more frequently at night, the wearer is generally in a prone position, such that their body weight tends to squeeze moisture out of the absorptive materials, allowing direct contact with the skin, particularly at or near such pressure points.

It is also believed that those of ordinary skill in the art have also failed to appreciate that booster pads may limit the effective capacity of the diaper they are deployed with. A booster, by absorbing fluid before the diaper core, is then the potential source of excess and non-absorbable urine and fluid which causes skin rashes. This may occur before the diaper 10 has an opportunity to absorb this urine and fluid that contacts the skin of the wearer.

In light of a much greater appreciation of the prior art over one of ordinary skill, the inventor has also come to realize that the ideal booster pad will initially absorb very little fluid, but rather pass it through to the diaper behind or below it, and only starts to absorb fluid and retaining excess moisture when the diaper is close to its total fluid or urine absorptive capacity. By the total absorptive capacity of a diaper 10 or related garments, we mean the total volume of fluid that could be absorbed based on the quantity of absorptive material if all this material were to absorb the maximum quantity of urine or fluid as if isolated from the other diaper components and adjacent absorptive material.

However, even reaching this ideal, there is an opportunity to further protect the skin, once the absorbent material in the diaper has reached its capacity.

Accordingly, the inventor has discovered that the inventive absorbent pads can be constructed in a manner that more thoroughly protects the skin from bodily fluids that might be squeezed out of the diaper 10, yet also allow the diaper to first absorb the fluid, even though it is at least partially covered by the absorbing booster pad 100. By such at least partial covering, we mean that the booster pad or absorbent garment insert 100 being placed into the ordinary diaper 10 or related incontinence garment is in skin contact, as it is above the absorptive layer in the diaper 10 or related incontinence pad.

In accordance with an embodiment of the present invention, such an absorbent garment insert or booster pad 100 may comprises an upper cover 110 and a lower cover 120 opposing the upper cover 110. The lower cover 120 is placed proximal to the upper porous layer 31 of the diaper, whereas the upper cover 110 is placed proximal to the skin of the wearer of the diaper that is fitted with the booster pad 100. An absorbent region 125 is disposed between the upper cover 110 and bottom cover 120. The absorbent member 125 may comprise a random or structured mixture of fluid absorbent and fluid non-absorbent filler. The absorbent member 125 preferably comprises primarily super absorbent polymer (SAP) particles 131 as the primary fluid absorbing material. Preferably, the SAP particles 131 are dispersed in a manner that leaves or creates channels for the initial flow of urine or fluid therethrough, toward the lower cover 120. The lower cover 120, being porous, allows such fluid to be absorbed in the diaper 10 after entering through the porous upper layer 31 thereof.

The absorbent garment insert or booster pad 100 will generally have a near rectangular shape with an aspect ratio of about 5 to about 30 and narrow width of greater than 1 inches about and less than about 6 inches. The thickness is preferably less than ½ inch, but more preferably less than ¼ inch, and most preferably less than about ⅛ of an inch. It some applications and uses it may taper in width toward the center and have rounded or bulging ends distance from the center.

The absorbent garment insert or booster pad 100 is generally planar to the extend it is meant to fold to the body surface contour when inserted into or and used as part of a disposal garment worn by the user and cover an area of the skin, however it need not be perfectly planar or have parallel top and bottom surface to provide this function. It may also be used with rubberized underware that is leakproof and can be washed, so that only the insert is disposed of. The absorbent garment insert or booster pad 100 may have larger dimension and be contoured so that is not rectangular as illustrated in several Figures. The term generally planar absorbent garment insert is also intended to embrace the same and equivalent constructions and materials that may also be incorporated as additional layers in a diaper 10, in which the insert or pad 100 is part of the diaper 10, and not a separate item of commerce from the diaper, but rather a component of a diaper.

As illustrated generally in FIG. 3C, among others, such a beneficial dispersion of the SAP particles 131 may be in a network of non-hydrophilic fibers 132 that form at least one layer 130' and/or 130" of absorbent material within the absorbent member 125. The absorbent member 125 may also contain other hydrophilic materials, such as fibers or mats of fibers, such as cellulosic fluff or tissues. Tissues should be understood to be thin compressed mats of fluid and urine absorbent fibers, such as cellulosic fibers that retain some of the initial strength when soggy or holding fluid. The absorbent member 125 may also comprise a plurality of additional layers forming a laminated structure between the upper cover 110 and lower cover 120. The upper cover 110 and lower cover 120 are sealed about a common perimeter 100p to contain the layer of absorbent material 130 and the additional layers in the laminate. The perimeter construction of preferred embodiments of the inventive booster pad or absorbent garment insert 100 is illustrated in FIG. 8-11. Suitable non-hydrophilic fibers 132 include without limitation polyolefin fibers, such as polyethylene, polypropylene, and polybutylene, as well as polyesters, polyamides, linear and at least partially aromatic polymers, such as polyethylene terephthalate and the like, as well as blends thereof, bicomponent and/or multi-component fibers and the like.

The absorbent member 125 is preferably layered or structured in a manner that mitigates the tendency for a high concentration of SAP particles 131 to form a solid gel film therewith, which would block the flow of fluid or urine to the diaper 10, or lower layer, such as layer 130", that also contains SAP particles 131. The absorbent member 125 may at least partially contain the SAP particles 131 in place and prevents migration into either the upper cover 110 and/or lower cover 120. The prevention of migration may be provided by one or more relatively thin layers of a porous membrane or fabric layer 140, such as the network of hydrophilic fibers 136, which is optionally tissue formed from natural fiber derived from wood products, woven textile and non-woven textiles.

FIG. 4A-4B illustrates the operative principle in which the booster pad or absorbent garment insert 100 having an upper cover 110 that is disposed proximal and opposing the skin 1, absorbs fluid or urine slowly, allowing the diaper core 21 to fill first, as shown on the left side of the diagram in FIG. 4A, as the SAP particles 131 in the diaper 10 absorbs urine or fluid and swell, they grow in size. However the absorbing layer or layers 130, 130' and 130" in the booster 100, more slowly absorb fluid or urine and at least initially do not form gel blocks such that the diaper 10 will substantially film and absorb fluid before the pad 100.

Another aspect of the invention illustrated in FIGS. 4A and 4B is the nature of the lower cover 120 which is illustrated as an aperture film. Since an overfilled diaper core 21 may readily release fluid or urine under pressure (shown as free fluid 9), the lower cover 121 is preferably a film that permits the downward flow of fluid from the direction of the core 130 but precludes the inward flow from below, that is upward from diaper 10. This precludes such free fluid 9 from the diaper 10 from reaching the skin 1 by migrating or over saturating the absorptive capacity of the booster 100. Such aperture films is disclosed in the following US patents, which are incorporated herein by reference: U.S. Pat. No. 7,601,414 (issued to J. W. Cree et al. on Oct. 13, 2009) and U.S. Pat. No. 3,929,135 (Issued to Thompson, H. A. on Dec. 30, 1975).

In these aperture films, the apertures 1204 are provided by an array of open cones 1201, which may have a frustoconical shape or at least any shape that provides a tapering in width from the opposing side, in which fluids and urine can exit the side of the sheet or film that form the lower cover 120 by flowing in the direction of double headed arrow 1215 from aperture 1202 at the cone base at the perimeter 1203 to a second aperture 1204 at the narrower cone apex. The second apertures 1204 are sufficiently small that fluid cannot flow through the lower cover 120 in the opposing direction. The aperture film 120 in FIG. 2D optionally has additional holes or aperture 1205 between or surrounding the cones 1201. These additional holes or aperture 1205 are also preferably small enough to prevent intrusion of fluid at least in the direction opposite arrows 1215. It should be appreciated the cones 1201 need not have a perfectly circular base at the apertures or pore 1202, and such tapering to the smaller aperture 1204 also need not be as circular hole. The combinations of apertures 1202 and 1204 may take on different shapes and orientation of shapes over the aperture film that forms the lower cover 120. The aperture film as the lower cover 120 may also deploy a combination of large scale apertures and smaller scale aperture. The mesh count of large scale apertures is optionally varied between 2/cm2 and 50/cm2 while the smaller scale aperture that are interspersed between or adjacent to the larger scale aperture and may have a mesh count of between about 20/cm2 and 200/cm2. The mesh count of the small scale apertures is between about 50/cm2 and 100/cm2. The relative ratio of small and large aperture counts and aspect ratios can be used to vary the stiffness and flexibility of the lower layer 120. The aperture film for lower layer 120 is optionally made of polypropylene, polyethylene, or some other polyolefin. Useful ranges for the diameter of the aperture or pores 1202 and 1204 to limit the flow of fluid to the direction of arrows 1215 are disclosed U.S. Pat. No. 3,929,135, however, to the extent the lower layer 120 is treated to vary the surface tension and wettability of urine and other fluids, the size of the apertures 1202 and 1204 may be varied.

The desired capacity and properties of the absorbent member 125 can be achieved with a wide range of component members. The SAP particles 131 can be spherical or roughly equiaxed particulates, acicular particles, platelets or fibrous in shape, and mixtures thereof. Further, along with shape, the SAP particles 131 can have various sizes with a total absorbency and absorbency rates as may be more opportune to provide for a controlled and gradual flow of fluid toward the diaper 10 porous outer layer 31, which will be disposed opposite the lower cover 120. At least some of the SAP particles 131 can be coated or partially coated to retard the rate of fluid absorption.

SAP particles 131 can absorb up to about 1200× their weight of water, and up to about 40-60× their weight in urine and other fluids, depending on the ionic or salt content. The rate and capacity for SAP particles 131 to absorb water as well as urine and other bodily fluids may depend on the cross-link density and the particle size, as well as the specific chemical composition. SAP's are now commonly made by the polymerization of acrylic acid blended with sodium hydroxide in the presence of an initiator to form a polyacrylic acid sodium salt (sometimes referred to as sodium polyacrylate). This polymer is the most common type of SAP made in the world today. Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile to name a few. SAP producers include EVONIK Industries, Nippon Shokubai, BASF, Sumitomo Seika Chemicals, SDP Global, and Yixing Danson Technology.

The layer 130 of absorbent material may be essentially free of hydrophilic fibers, such as organic natural fibers, pulp or fluff, including highly comminuted wood pulp, which is a form of cellulosic fiber. Such materials or fiber fluff may be formed by disintegrating wood pulp through splintering and fragmentation. Such fluff, being hydrophilic, is readily wetted by fluid or urine, and as such is capable of holding a large quantity of fluid between thin widely spaced fibers in the fluff mass. However, such swollen fluff will also readily release such fluid or urine under pressure. Accordingly, it is preferable that the layer 130 of absorbent material may be essentially free of hydrophilic fibers in either a separated form interspersed with SAP, or in the form of a compressed mat to form a tissue like layer. If any fluff or hydrophilic filler is used that permits the attachment of fluid in a liquid state, that is not bound as a gel to SAP 131, then it is preferably in a layer or portion remote from the upper layer 110.

When the SAP particles 131 are supported by a network of non-hydrophilic fibers 132, the non-hydrophilic fibers 132 may be provided as a discrete member that is metered or conveyed as a roll good from a web, or it may be formed as SAP particles is added to a construction formed by mixing SAP particles with some combination of cut fibers and/or continuous fibers and optionally adhesive, or providing a means for adhesive bonding, such as thermal or mechanical fusion and combinations thereof. This is generally illustrated in FIG. 3-7 and a method forming such an absorbent layer 130 is illustrated in FIG. 12A-13B. The transformation of this absorbent layer on absorbing fluid is schematically illustrated in FIG. 14. The SAP particles 131 may also be entrained between layers or strands of solidified hot melt adhesive to form a 3 dimensional network, as disclosed in U.S. Pat. No. 9,549,858 B2 (issued to Yang, C-Y. M. on 2017 Jan. 24).

Referring now to the embodiment of FIG. 3-7, a porous layer 140 may comprise separate discrete layers 130' and 130" each of which may comprise SAP particles 131 and a network of non-hydrophilic fibers 132. However, it may be convenient and useful to include in this laminated construction additional layers, like tissue 136 that contain at least some hydrophilic fibers, such as wood-derived or cellulosic materials. It may also be convenient and useful to deploy another layer of porous materials, such as woven or non-woven fabric, on opposite sides of layers 130' and 130".

As to any of the layers 130 of the type in which at least some of the SAP particles 131 is supported by a network of non-hydrophilic fibers 132, adhesives can be used to hold at least some of the SAP particles 131 in place. However, not all of the SAP particles 131 need to be physically or chemically bonded to the fibers 132'. Such adhesives can be water-soluble so they are readily applied as a spray without the need to deal with volatile solvent collection and recovery in manufacturing. While such adhesives may dissolve on contacting fluid or urine, the significant swelling of the SAP particles 131 may cause an expansion that fills the interstices so the fiber network 132 may more tightly contain at least some of the SAP particles 131, such as through mechanical interlock or interference. Conversely, the swelling SAP particles 131 may exert a force on any mechanical and/or chemical bonds of SAP particles 131 to the fibers.

The adhesive may also be a latex that at least partially cures or sets on drying, as well as thermoset or thermoplastic material, such as hot melt adhesive, that can bind the fibers 132 to each other, as well as the SAP particles 131 to at least some of the fiber 132. SAP particles 131 can also be applied to porous substrate in clusters that are adhesively bonded or are separated by being filled within preformed pockets, as disclosed in the following document: U.S. Pat. No. 9,056,033 B2 (Issued to Fenske W. on Jun. 16, 2015), U.S. Pat. No. 9,295,593 B2 (Issued to Van Malderen on Mar. 29, 2016), US2016/0175169 A1 (Bianchi E. G. et al. published Jun. 23, 16), US 2015/0164710 A1 (Ehkme, R. et al published Jun. 18, 2015), US 2003/0129915 A1 (Harris J. M. published Jul. 10, 2003), U.S. Pat. No. 6,068,620 (issued to Chmielewski, H. J. on May 30, 2000), U.S. Pat. No. 5,562,646 (issued to Goldman et al. on Oct. 8, 1996), US 2015/0065974 A1 (Michael D. et al. published Mar. 5, 2015) and WO2013/153235 A1 (Michaels, Dany published 17 Oct. 2013), all of which are incorporated herein by reference.

Other constructions and method of making an absorbent member or core 125 with a high loading of SAP particles are disclosed in EP 3153141A (Cipriani, A. et al published Sep. 29, 2016) and U.S. Pat. No. 7,232,300 B2 (issued to Walter J. et al. on Jun. 19, 2007), which are also incorporated herein by reference.

It is preferable that the network of non-hydrophilic fibers 132 or any other structure that is a porous membrane or fabric for receiving and supporting SAP particles 131 is a high loft non-woven material or mat 129 that provides an open structure, such as is illustrated in FIG. 12A. At least some of the fibers therein may provide the high loft characteristics in which many fibers are predominantly narrow and widely separated from each in both the thickness of the mat 129 as well as lateral dimensional. Such high loft material or webs are also preferably very compressible. Methods of making such high loft non-woven materials are disclosed in the U.S. Pat. No. 9,925,739 B2 (issued to Kauschke, M. et al Mar. 27, 2018), which is incorporated herein by reference. Webs of high loft non-woven materials may include a mixture of crimped fibers having wavy, curvilinear and/or irregular shapes to contribute loft and wide spacing between fibers. Such a high loft structure may include at least some longer or straight fibers that will tend to lay in a single plane or parallel planes, with some preference for a machine direction orientation, depending on how force is applied in assembling the fibers in a mat. The fibers can be bonded together with adhesives, or by thermal fusion, as well as pressure and combinations thereof.

It is also preferable that the high loft mat 129 is formed with at least some proportion of fibers that have a thermoplastic outer layer, such as bi-component synthetic fibers in which a core fiber element is coated or adjacent to a lower melting point fiber element. Bi-component fibers can be crimped, twisted, bent or curved and the like to contribute to the loft, as well as bond to themselves and other fibers to increase the strength and mechanical integration of the mat or sheet. Such fibers, when used to form high loft mats, may facilitate thicker mats by the lamination of multiple layers, such as by merging webs of materials, which can then be attached to each other by thermal lamination, and avoid the further addition of adhesives. A thermal lamination process may be advantageous to the extent it compresses the fiber network around the SAP particles 131 and reduces the bulk of the construction by compressing the high loft mat 129. The high loft mat 129 may be at least partially reduced in thickness as the lower melting point component of the fibers fuses to both other fibers and SAP particles 131, closing and reducing the size of the inter-fiber interstices around the SAP particles 131, and more tightly binding the SAP particles 131 therein.

The SAP particles 131 can be mechanically infiltrated into high loft mats or other non-woven fiber composites or assemblies by vibration, vacuum, and electrostatic charging, as disclosed in U.S. Pat. No. 5,552,012 (issued to Morris, M. C. et al. on Sep. 3, 1996) and U.S. Pat. No. 6,972,011 B2 (Made, S. et al. issued on Dec. 6, 2005) which is also incorporated herein by reference. SAP particles 131 may be distributed into a preformed web of bonded, fused or entangled natural or synthetic fibers, but can also be co-deposited with such a web as it is formed such that the space between the bonded or entanglement non-hydrophilic fibers 132 provides an open mesh of interstices. SAP particles 131 can also be entrained in a network of high loft fiber when the web is formed by a process of air blowing fibers mixed with SAP 131 particle and adhesives to bind them together.

In a preferred embodiment of the invention, the SAP particles 131 may be selected to absorb urine more slowly than the SAP particles found in conventional diapers 10, such as to enhance the effect schematically illustrated in FIGS. 4A and 4B. More particularly, the construction of the booster or absorbent garment insert 100 in FIG. 2B, in which the SAP particles 131 are distributed in separate sub-layers 130' and 130", each sub-layer may contain a form, concentration or type of SAP particles 131 that is adapted to the purpose of having the upper sub-layer 130' more slowly absorb fluid than the lower sub-layer 130". For example, sub-layer 130' may contain SAP particles 131 that slowly absorbs urine because it is bonded to the non-hydrophilic fibers with different adhesive than sub-layers 130", as for example the adhesive in one layer may dissolve or decompose more slowly than the other adhesive, or may be present in a greater concentration and hence, block some surface are of the SAP particles 131 in the different layers 130' and 130". Examples of preferable absorption of SAP particles of different types is disclosed in U.S. Pat. No. 5,728,808 (Issued to Gustafsson, L. et al. on Mar. 17, 1998), which are incorporated herein by reference.

The SAP particle 131 in any layer may be comprised of a mixture in which sub-sets of the SAP particles in the mixture have different absorption rate due to their differences in size and/or chemical composition, which can include a difference in degree of cross-linking and/or molecular weight of the polymers used in the different SAP particles 131.

Preferably, at least about 5% by weight of the SAP particle 131 should have such differences in one or more size and/or chemical composition to have different absorption rates. More preferably at least 20% by weight of the SAP particles 131 should have such a difference. Most preferably, at least about 40% by weight of the SAP particles 131 should have such a difference.

Further, the difference in absorption rate of the SAP particles 131 may differ by about 50%, but more preferably differs by about 100% and most preferably differs by about 200%. The upper and lower sub-layers 130' and 130" may vary in the ratio and type of SAP 131 particles they contain.

It is believed that such differences in absorption rates enhance the fluid absorbing capacity of the core 130 by providing pathways for fluid to ingress between the SAP particles 131 that absorb fluid quickly, which are provided by the hard and less pliable SAP particles 131 that more slowly absorb fluid. This may prevent the growing SAP particles 131 that absorb water from colliding and sticking as they swell which will tend to block the rate at which the fluid can migrate through the absorbent member 125 to exit toward the porous perimeter 100p or lower layer 120 of the booster pad or absorbent garment insert 100 to be initially captured in the absorbent materials of the diaper 10.

Figure 6:
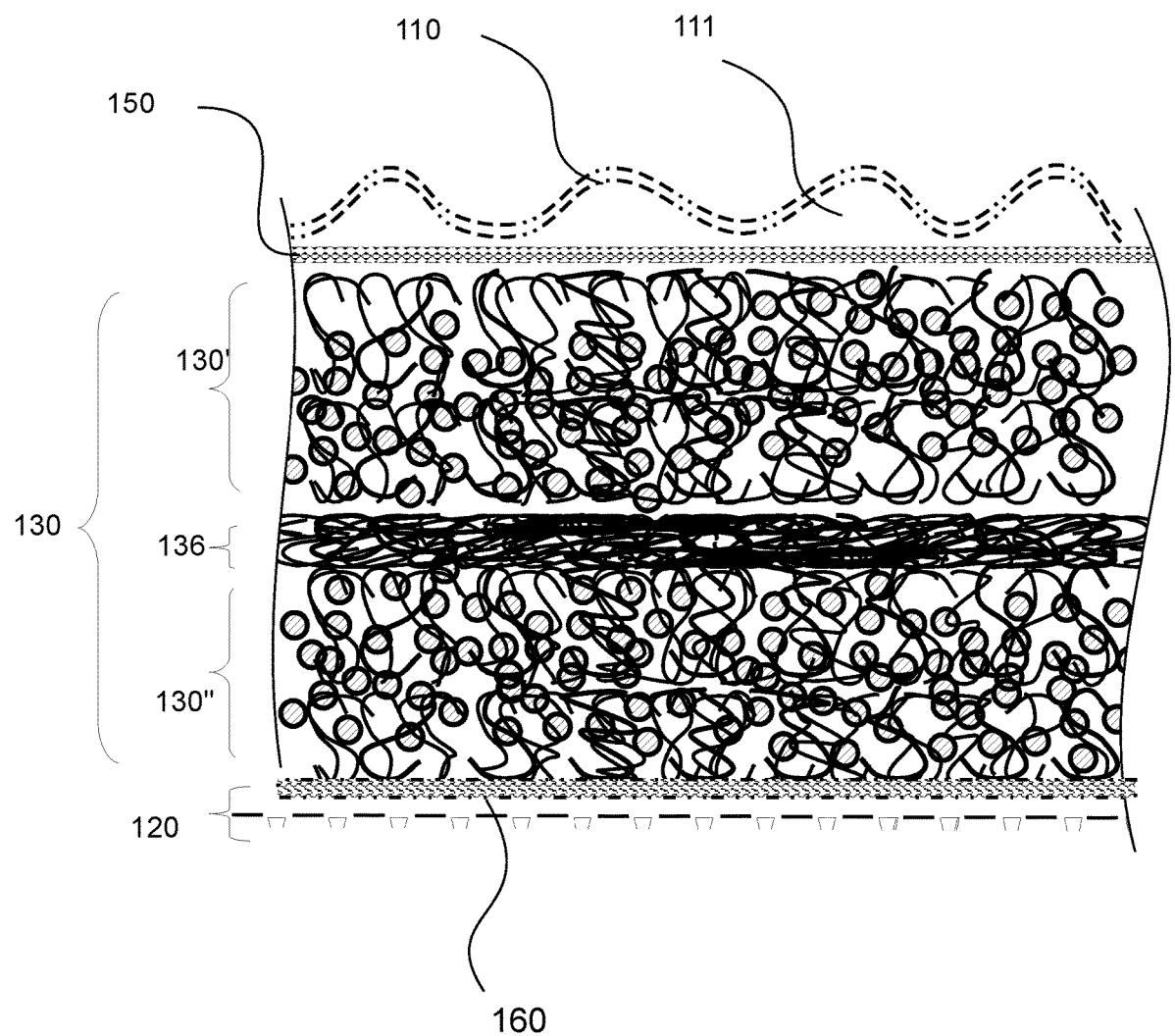
FIG. 6 is a schematic cross-sectional elevation view of the layers of materials used in absorbent pads according to another embodiment of the invention.

Referring to FIG. 6, another preferred aspect of the invention is the placement of another porous layer 160 between the bottom or lower layer 120 and the absorbing layer 130 or 130". Layer 160 should have pores that are small enough to allow the outward flow of fluid to the aperture film as layer 120 but to retain both the dry and swollen SAP particles 131. Absent layer 160, any SAP particles 131 that is extruded from the containing layer, such as layer 130", as it swells could clog the apertures in the film layer 120.

Figure 5:
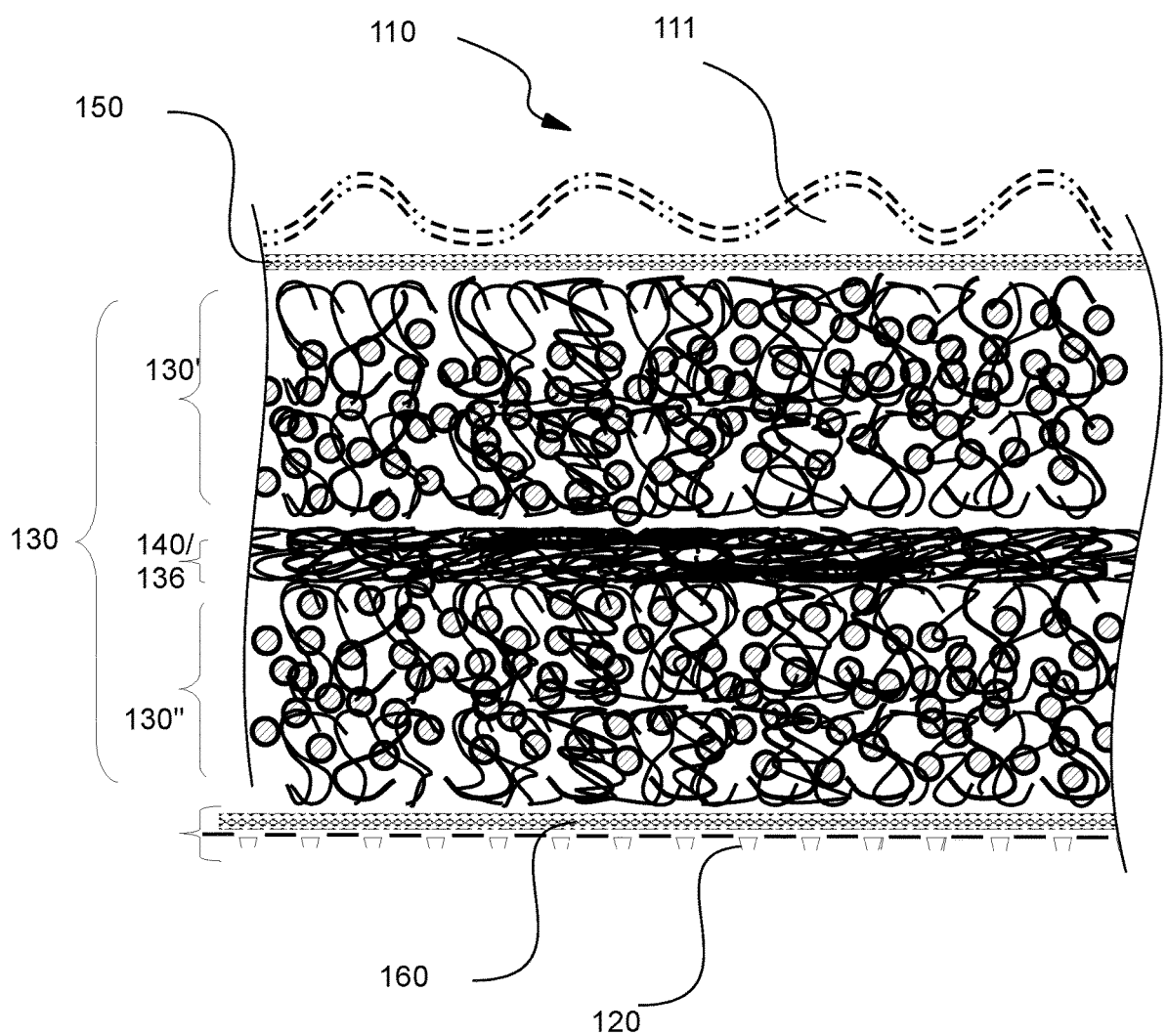
FIG. 5 is a schematic cross-sectional elevation view of the layers of materials used in absorbent pads according to another embodiment of the invention.
Figure 7:
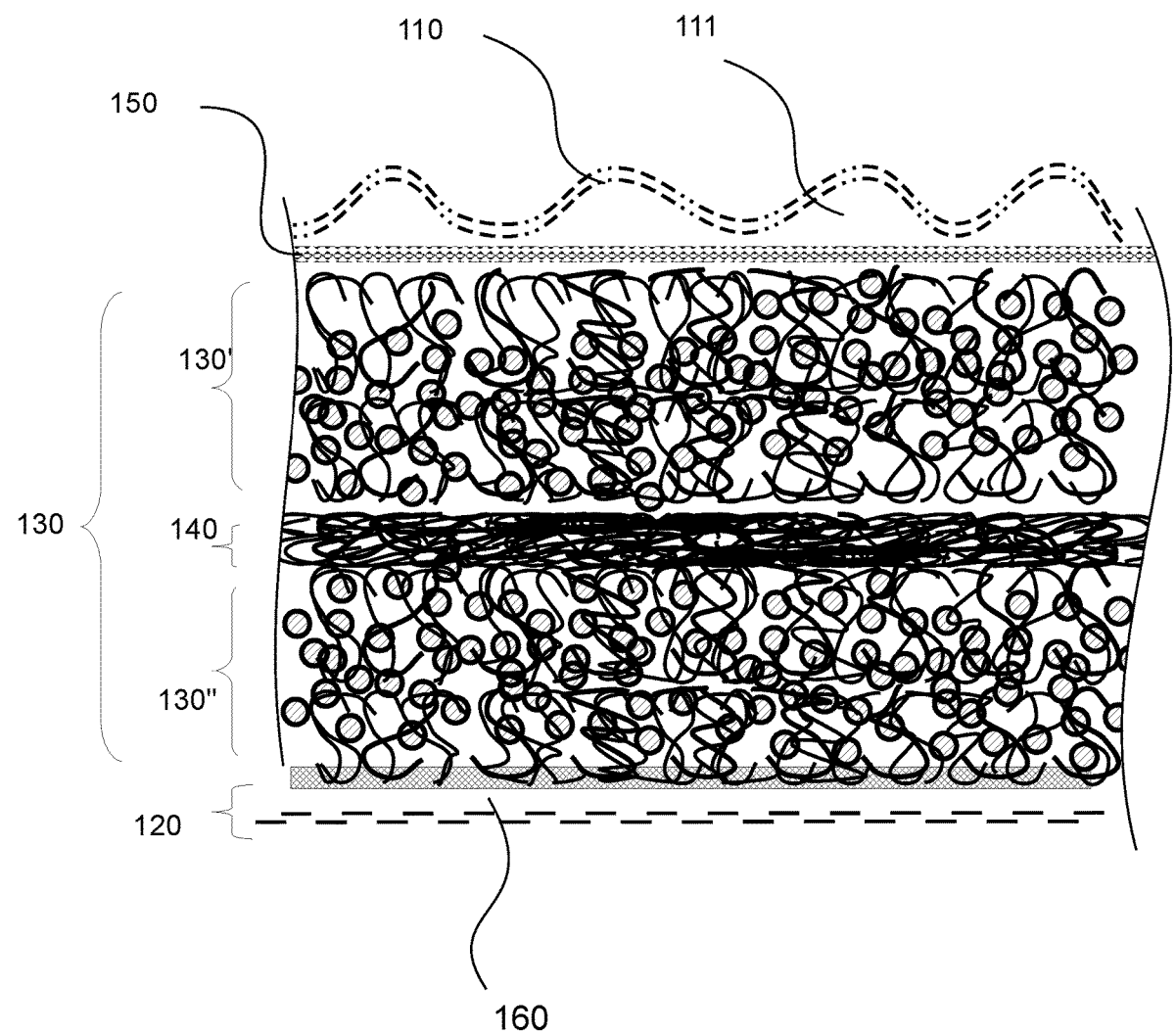
FIG. 7 is a schematic cross-sectional elevation view of the layers of materials used in absorbent pads according to another embodiment of the invention.

Another preferred aspect of the invention that is illustrated in FIG. 5-7, among others, is the nature of the porous fabric that forms the upper cover 110. Upper cover 110 is preferably a non-woven fabric having an undulated self-supporting structure that defines a matrix of adjacent cavities 111. The non-woven fabric 114 is formed from fibers or mixtures of fibers. The coherent nature of the non-woven fabric is provided by the physical entanglement and/or fusion bonding of the fibers therein. Methods of making such non-woven fabrics may be by any method of creating a non-woven fabric that is generally planar and then embossing a 3 dimension pattern with a die or tool having an aspect of the undulating shape of the self-supporting structure of non-woven fabric 114. The embossing may be done by the process disclosed in U.S. Pat. No. 8,425,729 B2, which is also incorporated herein by reference. Alternative methods and specific structures for non-woven webs have also been disclosed in US Pat. Appl. No. 2017/025860 A1 (published Sep. 14, 2017, Rosati, R. et al.), as well as U.S. Pat. No. 6,344,102 B1 (issued to Wagner, W. on Feb. 5, 2002), which are also incorporated herein by reference.

In a preferred embodiment schematically illustrated in FIG. 5, the upper cover 110 is a 3D non-woven and the lower or bottom cover 120 is an aperture film. FIG. 5 also illustrates layer 160 that is laminated between layer 130" and 120. Layers 150 and 160 cooperate to retain dry and swollen SAP particles 131 between the layers 110 and layers 120. In the case of layer 150, the natural loft of the 3D layer 110 provides cavities 111, so space remains between the wet absorbent materials such that the wearer's skin stays dry. Further, the SAP particles 131 preferably doe not migrate within the cavities 111 when swollen. Layer 160 similarly has pores sufficiently small to prevent the downward migration of SAP particles 131 in layer 130", to preclude any clogging of the holes or pores in the layer 120, which is preferably an aperture film, such as with apertures that extend as cones out of the plane of the film, to allow the flow of fluid or urine from the wider base of the cone to the opposing side or apex, while blocking the entry of fluid or urine into the cones from the narrow side.

It should be appreciated that as many of the benefits of the inventive booster 100, when used in a diaper 10, are achieved by the nature of the bottom or lower layer 120, the absorbent core 130 can take many forms known in the prior art or subsequently discovered. However, with these many options it is generally preferred that core 130 have good strike-through properties and does not gel block as the SAP particles 131 expands to its fullest capacity. Strikethrough simply means the rate at which urine will permeate through as it is absorbed by the absorbing components, such as SAP particles 131 and any hydrophilic, non-hydrophilic and hydrophobic fibers. It should be appreciated that such booster pads or absorbent garment inserts 100 will expand the capacity of some diapers 10 more than others, to the extent that the diaper 10 will absorb and distribute fluid or urine faster relative to the absorbent core 125 as may be limited by the rate at the SAP particles 131 in the core 125 can absorb fluid, swell and expand. Hence, it may be advantageous that the process of the forming the laminate of SAP particles 131 and fibers in the core partially coat at least some of the SAP particles 131 with thermo-plastics or adhesives that retard the access and swelling by fluid or urine. It should be appreciated that any of layers 140, 150 and 160 can be ADC or ADL materials.

As many types of non-woven fabrics that contain or restrain a matrix of absorbent material with a high loading of SAP particles 131 can be used in the absorbent core 125 of the boaster pad or absorbent garment insert 100, more preferred embodiments will be referred to by the general properties or composition and the area density in grams per square meter.

Figure 8:
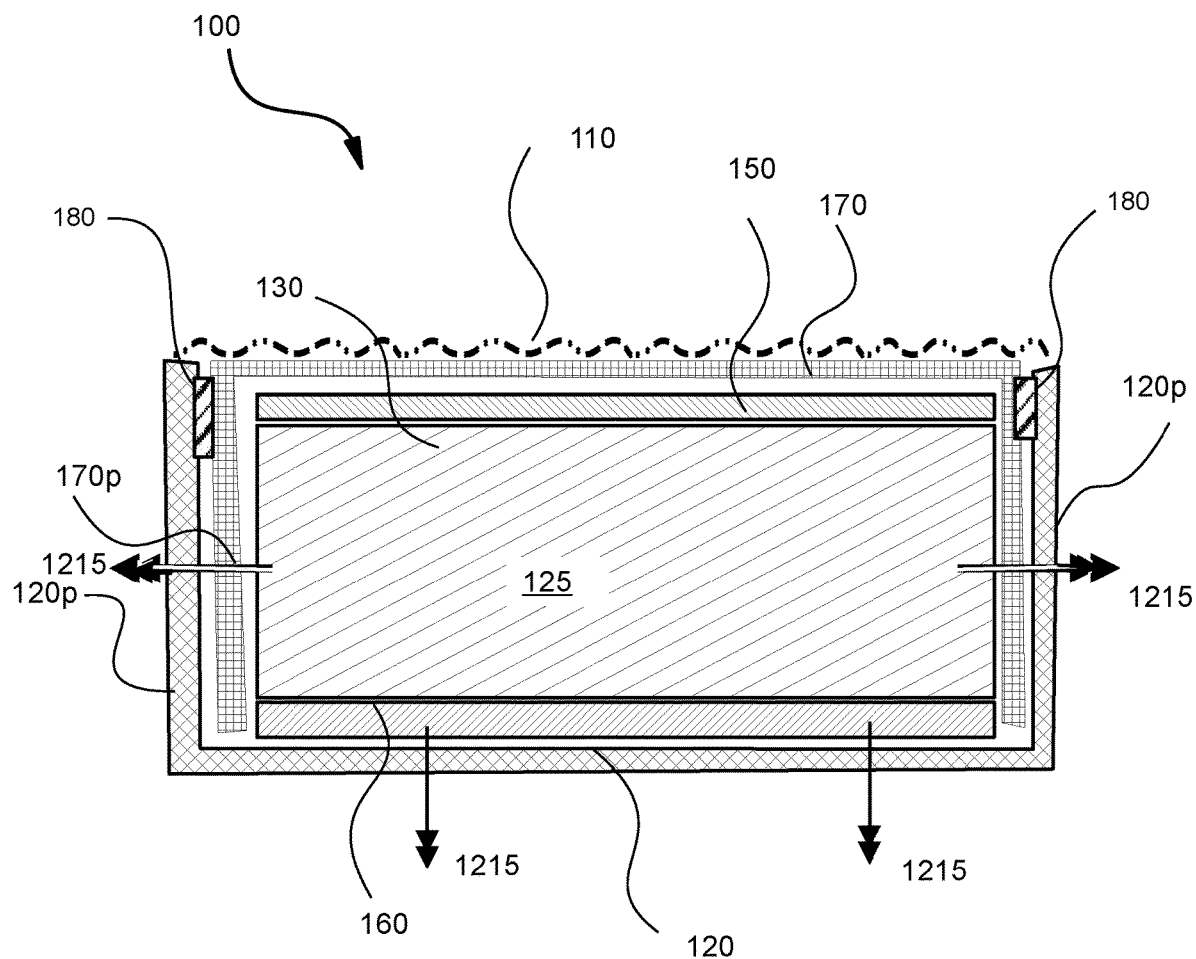
FIG. 8 is a schematic cross-sectional elevation according to the orientation in FIG. 2B, to illustrate additional aspects of the invention.

FIG. 6 illustrates an embodiment in which the upper cover 110 is a 3D non-woven having a weight of 25 grams per meter squared (gsm), layer 170 is a 13 gsm polypropylene porous non-woven fabric wrapper goes around pad sealed on back, as in FIG. 8. Layer 136 is a dense compressed pulp mat of hydrophilic fibers having a weight of about 50 gsm. Layer 130' is a 50 gsm is a high loft mat formed from a mixture of bi-component fiber, such as with a polypropylene or polyethylene terephthalate (PET) core of a higher melting and softening point than polyethylene on the outer surfaces thereof. Layer 130' contains SAP particles 131 that absorbs fluid or urine, particularly urine, slower than SAP particles 131 contained in a similarly formed layer 130', which also has a weight of 50 gsm. Layer 160 is a 25 gsm porous non-woven synthetic fiber material. Layer 120 is a 25 gsm apertured film. It should be noted that layer 140 can be substituted with a non-hydrophilic porous non-woven fabric or any thin flexible porous member. Layer 140 can be omitted. Any layer can be split into additional layers. The SAP particles 131 can be deposited in layers 130' or 130" in patterns or channel to leaves lateral gaps for the more rapid strike-through of fluid or urine directly to the diaper 10.

FIG. 7 is another embodiment similar to that of FIG. 6, in which the aperture film 120 is replaced with a porous non-woven fabric capable of allowing the flow of liquid in both directions.

It should be appreciated that the relative absorptive capacity of a diaper or booster is proportion to the effective weight of the fluid or urine absorbing component to the other materials of construction, as polymeric materials have comparable densities. By effective weight, we mean the mass of absorbing materials that will absorb fluid or urine and not be blocked from fluid or urine by the gelling of some of the SAP particles 131.

Other preferred embodiments may contain from about 40 to 80% SAP particles by weight as compared to the other constituent, as shown in the following Table I, in which layer 150 is formed from 2 layers, 150' and 150" with different densities and composition as noted below:

TABLE I

| Layer | Example No. 1 | | Example No. 2 | | Example No. 3 | |
|---|---|---|---|---|---|---|
| | Weight of NW in gsm | Weight of SAP particles in gm in the layer per SM | Weight of NW in gsm | Weight of SAP particles in gm in the layer per SM | Weight of NW in gsm | Weight of SAP particles in gm in the layer per SM |
| 110 (3D non-woven (NW) fabric) | 25 gsm | | 25 gsm | | | |
| 150' | 13 gsm | | 13 gsm | | | |

TABLE I-continued

| Layer | Example No. 1 Weight of NW in gsm | Example No. 1 Weight of SAP particles in gm in the layer per SM | Example No. 2 Weight of NW in gsm | Example No. 2 Weight of SAP particles in gm in the layer per SM | Example No. 3 Weight of NW in gsm | Example No. 3 Weight of SAP particles in gm in the layer per SM |
|---|---|---|---|---|---|---|
| polypropylene NW 150" compressed matt of hydrophilic fiber pulp | 50 gsm | | 50 gsm | | | |
| 130' high loft matt of bicomponent fibers | 50 gsm | 210 gm | 50 gsm | 300-600 gm | 129 high loft matt of bicomponent fibers, 50 gsm | 300-600 gm |
| 140 NW | 25 | | | | | |
| 130" (same as 130') | 50 gsm | 210 | None | None | compressed matt of hydrophilic fiber pulp 50 gsm | |
| 160 dense synthetic fiber or NW fabric | 25 gsm | | 25 gsm | | 25 gsm | |
| 120 (aperture film) | 25 gsm | | 25 gsm | | 25 gsm | |
| Weight of SAP particles as a % of total | | 70% | | 58-73% | | 58-73% |

Another aspect of the invention is the manner in which the upper layer 110 and a lower cover 120 may meet, merge, seal, bond or overlap in the perimeter region 100p, as illustrated in FIG. 8-11. In these preferred embodiments, the upper cover 110 is a preferably a 3D non-woven fabric and the lower or bottom cover 120 also wraps around the core 130 at the perimeter 100p so that fluid or urine may flow downward and laterally out into a surrounding diaper 10. The lower or bottom cover 120 may be affixed to the core 130 or the upper cover 100 with one or more applications of an intermediate adhesive layer 180. In these and other related alternative embodiment of the booster 100, fluid or urine can readily flow through a porous perimeter 100p, in which the upper cover 110 and/or lower cover 120 may wrap laterally along the side of the absorbent core 125. Double-headed arrows 1215 illustrate the preferred directions for fluid or urine to flow to maximize the filling of a diaper and avoid having the booster 100 block some of the diaper'10 absorbent capacity. The perimeter 170p of layer 170 aids in precluding dry and swollen SAP particles 131 from extruding laterally as they swell, and thus prevents clogging pores in perimeter 100p.

It is preferable in these embodiments that perimeter 100p and 170p is porous, so that upper layer 110 and any layers below, such as sub-layer 150 can spread fluid or urine to the side or perimeter 110p, resulting in at least some of the fluid or urine can be shed to the sides before entering the absorbent core 125. It is preferable that the porous perimeter 100p is formed by an overlapped wrapping of the upper or lower exterior layers or most adjacent sub-layers. Such wrapped layers and sub-layers can be bonded to each other by various means, such as adhesives, sonic welding, spot welding, stitching and the like to contain the absorbent core 125.

In the embodiment of FIG. 8, adhesive 180 can be applied in stripes in the machine direction during a web lamination process so that transverse direction folding at the perimeter 100p of overlapping layers disposes the adhesive 180 between a side 170p of the porous layer 170 and upward vertically extending side 120p of the porous bottom layer 120. The adhesive 180 only partially blocks the lateral channel formed at the perimeter 100p, by the overlap of perimeter 180p and perimeter 170p.

Figure 9:
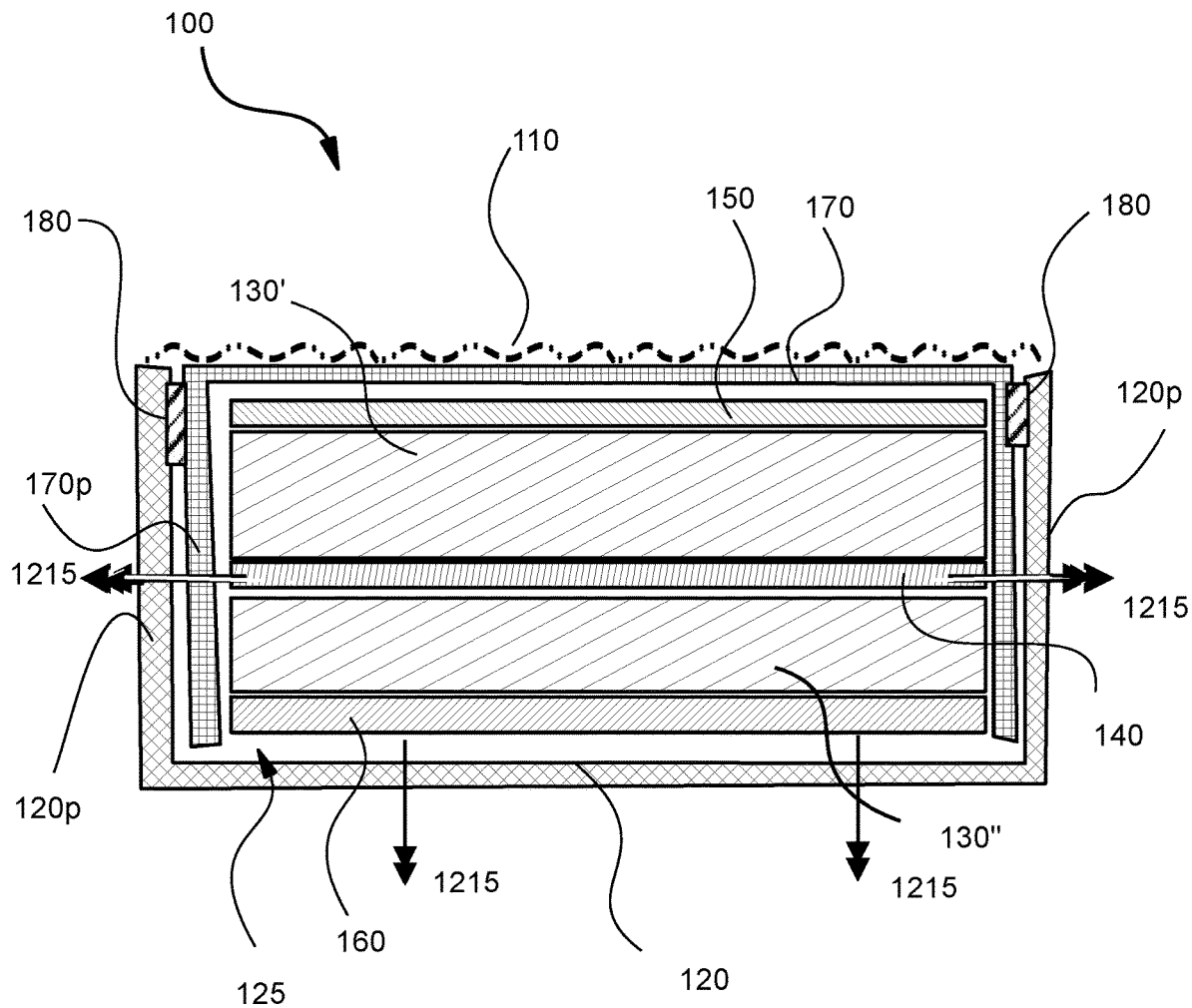
FIG. 9 is a schematic cross-sectional elevation according to the orientation in FIG. 2B, to illustrate additional aspects of the invention.

In the embodiment of FIG. 9, the absorbent core 125 has a sub-layer 130' and 130" in which a lower porous layer 160 is above the bottom layer 120, and a porous sub-layer 150 wraps around the lateral side of the sub-layers 130' and 130", such that layer 170 and 120 are bonded adjacent to upper layer 110.

Figure 10:
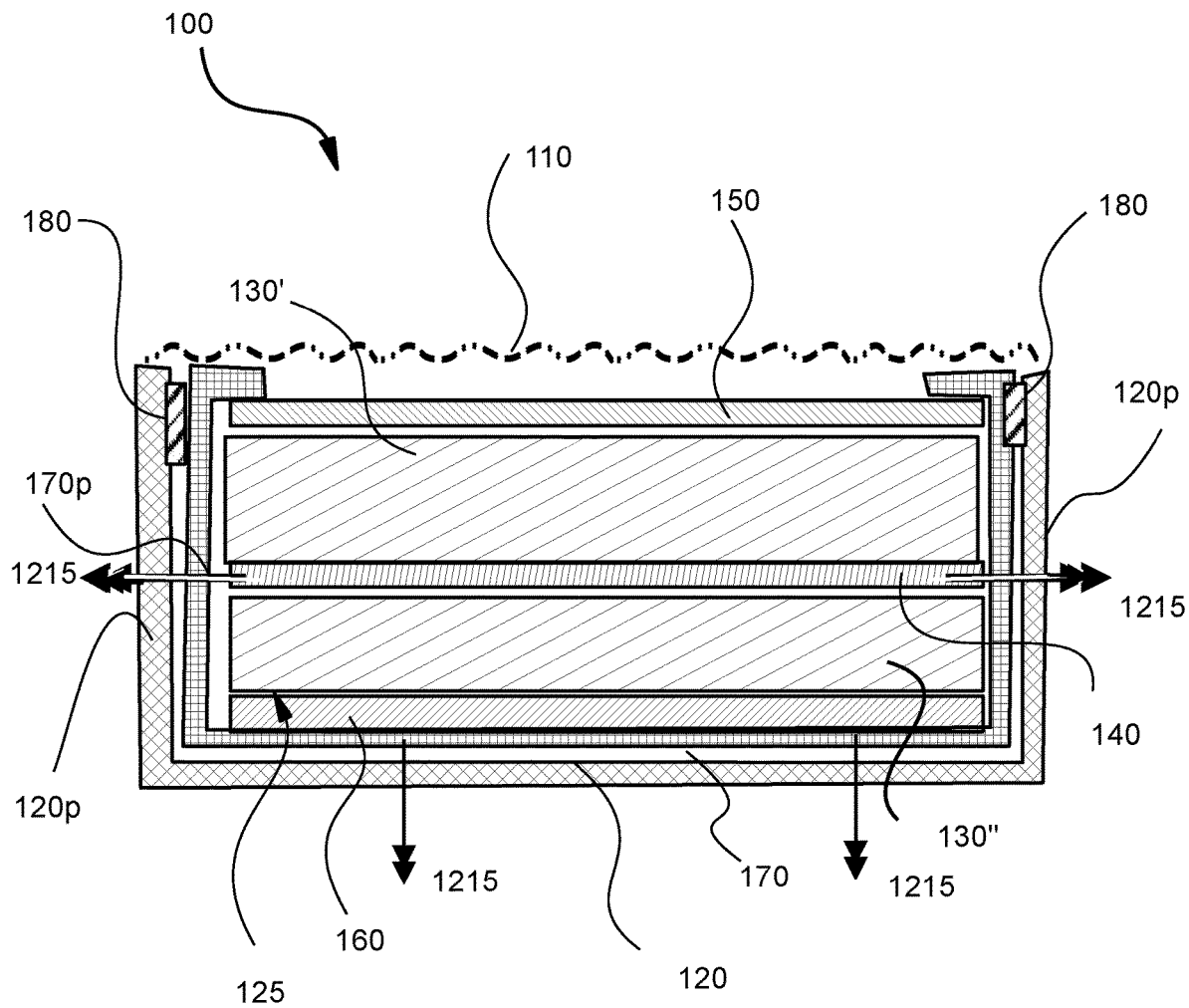
FIG. 10 is a schematic cross-sectional elevation according to the orientation in FIG. 2B, to illustrate additional aspects of the invention.

FIG. 10 illustrates an embodiment with an absorbent core 125 having sub-layer 130' and 130" in which a lower porous layer 170 extends around the bottom of sub-layer 130" and the lateral sides of both sub-layers 130' and 130". The edges of sub-layer 170 that cover sub-layer 150 are in turn covered by the upper layer 110, which can be attached to the edges of layer 170, as well as the upper edges of layer 180 so that the perimeter portion 180p of layer 180 overlaps the perimeter 170p of layer 170.

In another embodiment of the invention, illustrated in FIG. 11A, the bottom or lower layer 120 is partially covered on the outer surface with an adhesive material or layer 190 for affixing to the interior of a diaper 10. This adhesive layer 190 may be covered by a release film 195 or other cover so that it does not stick or adhere to other materials until it is placed inside the diaper. Such adhesive layer may include without limitation pressure sensitive adhesives, as well as hook and loop type mechanical fasteners. A more preferably configuration (FIG. 11B) of the adhesive layer 190 is as three adjacent stripes 191, 192 and 193, which may be about 1-2 mm wide and separated from the adjacent stripe by about 4-6 mm, to provide a total width of about 11 mm or about 18 mm, or about ¼ to ¾ of an inch. The adhesive material 190 may be selected for the ability to provide firm bonding to non-woven fabric that form the interior of the diaper 10. Micro-hook type fasteners can strongly couple to non-woven fabric by mechanical interlocking very rapidly once the contact force is sufficient to push the micro-hooks in between the fiber strands of the non-woven fabric.

FIG. 12A-13B illustrates the primary steps in forming an embodiment of the invention in which the SAP particles 131 are added to a high loft mat of entangled, bonded and/or compressed fibers 129 that has interstices to entrap the SAP particles 131 as shown in FIGS. 12B and 13B.

FIG. 12A shows the open nature of the high loft mat 129 before the filling with the SAP particles 131, which can be feed by gravity or air pressure, as well as mechanical spreading and filling, such as by agitation, vibration and the like to provide filled layer 1220.

A lower layer, 1210, which is optionally a dense compressed mat 130' of hydrophobic fibers, such as a non-woven fabric, or tissue formed form hydrophilic fiber or pulp, can be attached or bonded in this process to retain the SAP particles 131 before or after they enter on the initially upper side 129a to form a filled high loft mat 1203. The pores or opening in the mat 130' are small enough to retain the SAP particles 131. This attachment or bonding can be achieved by first applying a very thin non-continuous layer of thermoplastic hot-melt adhesive 1219 to the compressed mat 1210 before it is brought in contact with the high loft mat 129.

As illustrated in FIGS. 13A and 13B, depending on the density of the mat 129 and the size and concentration of the SAP particle 131, it may not be necessary to seal the initially upper side 129a of the high loft mat 129 with the lower layer 1210 until after it is filled with SAP particle 131, as the penetration of the SAP particles 131 may be limited to an upper portion 1220' as shown in FIG. 13B. Hence, as also shown in FIG. 13B, the mat 1210 is attached with adhesive 1219 to the same the initially upper side 129a of the high loft mat 129 after it receives the SAP particles 131, so that the assembly 1203' can be inverted so more SAP particles 131 can then be added to the opposing open side 129b.

Figure 14A:
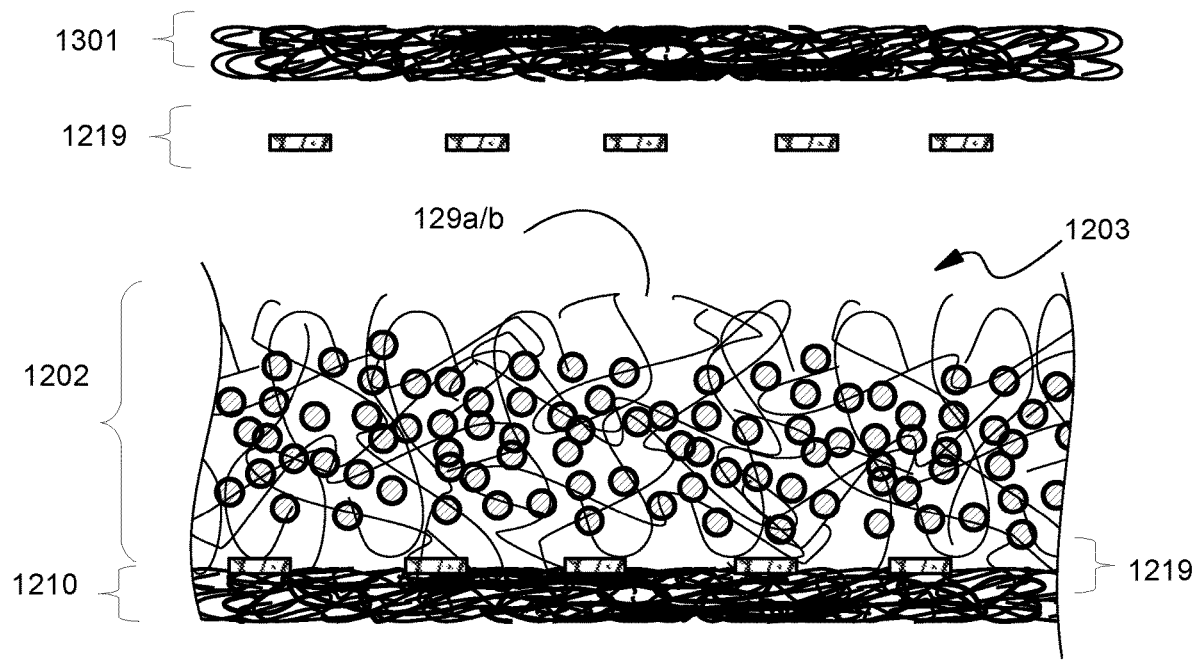
FIGS. 14A and 14B are schematic diagrams illustrating steps in a method applying additional layers to the absorbent core formed in the steps illustrated in FIGS. 12A and 13B, so as to form the other embodiments.
Figure 14B:
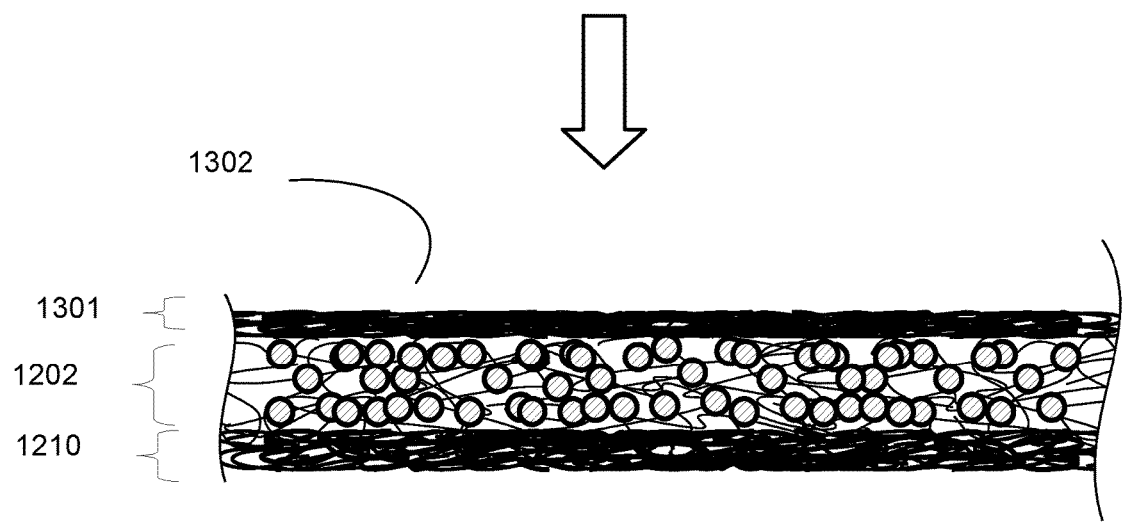

FIG. 14A-B illustrate a continuation of the process from FIG. 12B or 13B in which a covering layer 1301 is disposed on the SAP particles 131 filled high loft mat 1203 from side 129b or 129a. FIG. 13B shows a resulting compressed sub laminate 1302 formed from the absorbent filled high loft mat 1203 when the top layer 1301 is applied with pressure, such as from a top roller or nip roller when the layers 1301 and 1203 are conveyed as separate web that join as the supporting roller approach at a nip region. Additional layers or wrapping can be applied sequentially in a continuous process or another sub-laminate can be joined so that the layer count increase by at least two from the sub-layer or laminate 1302 in FIG. 14B. These layers and compressed sub-layers can be joined by adhesive, heat, friction or ultrasonic welding, and the like. Adhesive 1219 can be applied in a continuous process as film, such as by curtain coating, or sprayed on in selected regions to form a pattern, or sprayed to cover the breadth of the laminated layers. An adhesive that is capable of filling pores in a layer should be applied in the minimum amount, as in patterns to maintain vertical porosity and fluid or urine flow in the absorbing layer 1202. It may be preferable to avoid the application of the adhesive directly to the high loft fiber mat 1203 or the 3D non-woven layer 110, but rather to the more compressed or dense later 1210 or 1301, to minimize the opportunity to flow, diffuse and spread to avoid clogging pores and interstices intended for fluid flow the SAP particles 131.

Figure 15:
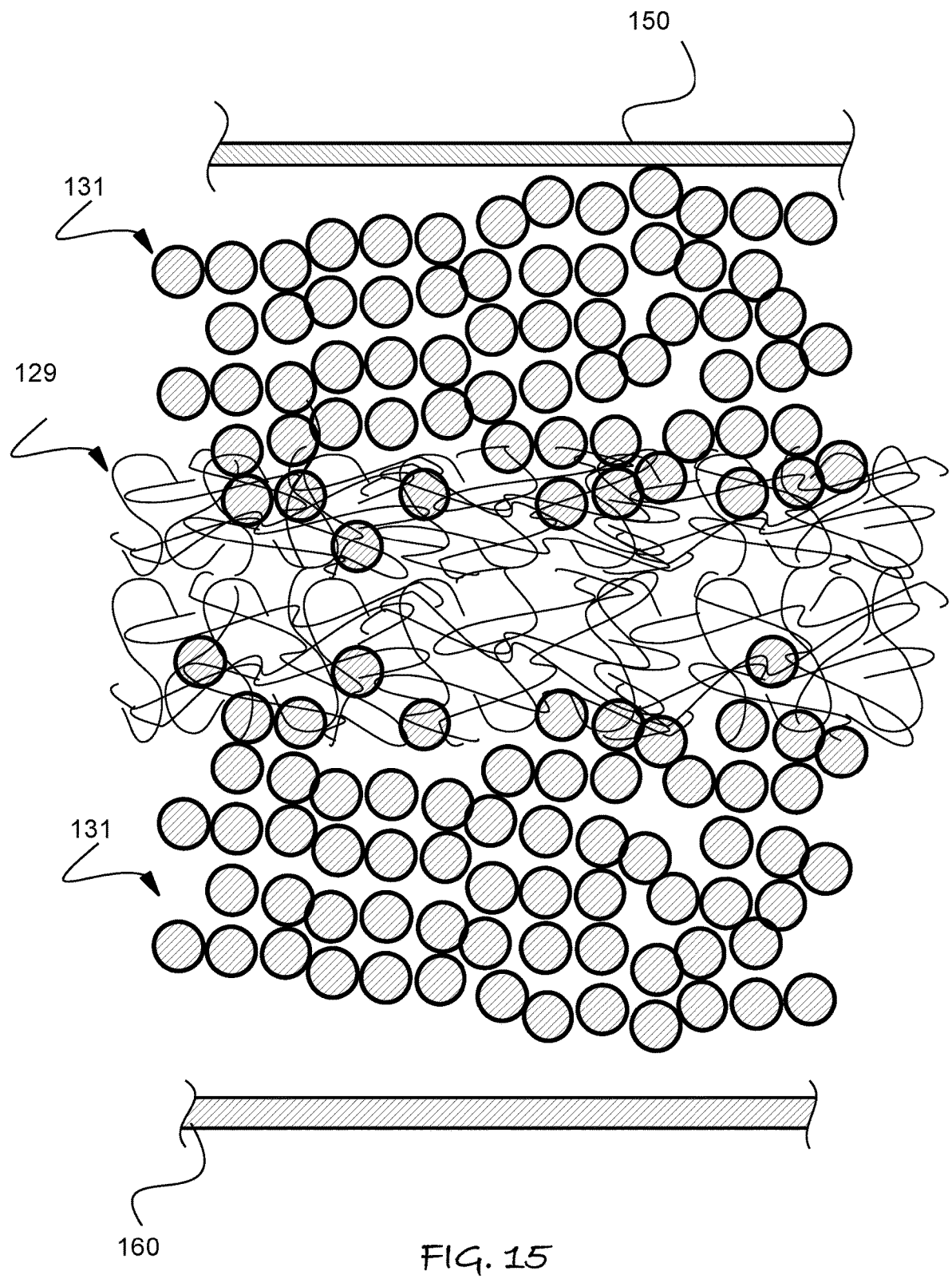
FIG. 15 is a schematic cross-sectional elevation of the transformation of a select embodiment of the invention as the absorbent core becomes saturated with fluid absorbed therein.

Not wishing to be bound by theory, FIG. 15 is intended to illustrate schematically in a cross-sectional view the transformation of the various other embodiments as the booster pad or absorbent garment insert 100 approaches a maximum absorbent capacity that is limited by the total volume of the SAP particles 131 therein.

It is believed the combination of the SAP particles 131 bound by compression in the otherwise high loft mats 1302 of FIG. 13B have a minimum tendency to gel block as a result of a gradual release of the swollen SAP particles 131 from the fiber mat 129 as it expands, as schematically illustrated in FIG. 15. The SAP particles 131 may increase in diameter 10, 20 or 30 or more times their initial diameter when saturated with water, urine, and similar aqueous body fluids.

The bonding of the SAP particles 131 in the fiber mat 129 as illustrated in FIG. 12A-14B is likely to be a stochastic process, and since the high loft matt has compressed as shown in FIG. 14B, at least some of the SAP particles 131 have become unbounded as it swells and they extrudes through the mat layer 129, while some smaller amount of swollen gel volume remains in the mat layer 129. It is believed that any unbound SAP particles 131 will likely swell first. As they swell and then become released from the mat layer 129, this creates new channel or passages for the flow of liquid to the SAP particles 131 that are more deeply disposed within the mat layer 129, of which the more tightly bound gelling SAP particles 131 are expected to release and extrude outward from the mat layer 129 last, depending at least in part on the original proximity to the outer surface 129a or 129b from which it entered (129a in FIG. 12A). It is believed that SAP particle 131 will tend to release in the direction in which they are infiltrated in the mat layer 129. That is if they are added from one side 129a, they will tend to release from that side 129a, as at least some unbound SAP particles 131 are more likely to be found proximal to the same surface, and hence escape in the reverse direction from which it was deposited for further infiltration. Thus as the upper layers of SAP particles 131 extrude, they provide free space for the compressed mat 1202 formed from mat layer 129 to expand and then de-bound and/or release the underlying SAP particles 131 to extrude in the same direction.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

What is claimed:
1. A system comprising:
 a. an absorbent garment having an interior surface configured with a fluid porous inner surface that is configured to face a wearer, the inner surface being opposed by an fluid impervious outer surface configured to face outward from the wearer and a fluid absorbent core disposed between at least between a portion of the inner surface and outer surface,
 b. an insert capable of being fitted between a portion the wearer's body and the interior surface of the absorbent garment, the insert comprising;
  i. an upper cover that is fluid porous,
  ii. a lower cover opposing the upper cover, iii. a plurality of layers of an absorbent filling material consisting essentially of super absorbent polymer (SAP) particles dispersed in a network of non-hydrophilic fibers, iv. wherein the upper cover and lower cover are sealed about a common perimeter to contain the absorbent filling material in an interior cavity, and c. wherein the lower cover is an apertured film comprising an array perforations, each perforation in the array having a frustoconical shape with an open apex spaced apart from an open base, the base having a larger diameter than the apex and being closer to the absorbent filling material than the open apex.

2. The system according to claim 1 wherein the insert has a generally rectangular shape with an aspect ratio of between about 5 to about 30 and a width of greater than 1 inch about and less than about 6 inch.

3. The system according to claim 1 wherein the the lower cover has an exterior surface facing away from the upper cover, the exterior surface being adapted to be adhered on one or more portions thereof to the interior surface of the absorbent garment.

4. The system according to claim 1 wherein the lower cover has an exterior surface facing away from the upper cover and further comprising one or more regions of pressure sensitive adhesive on the exterior surface of the lower cover.

5. The system according to claim 4 in which the pressure sensitive adhesive region on the exterior surface of the lower cover are covered with a removable release film.

6. The system according to claim 1 wherein the one or more regions of pressure sensitive adhesive of the insert are adjacent stripes.

7. A generally planar absorbent member comprising:
an upper cover,
a lower cover opposing the upper cover,
a plurality of layers of an absorbent filling material consisting essentially of super absorbent polymer (SAP) particles dispersed in a network of non-hydrophilic fibers,
wherein the upper cover and lower cover are sealed about a common perimeter to contain the absorbent filling material in an interior cavity, and
the upper cover and the lower cover comprising a porous fabric,
wherein the network of non-hydrophilic fibers expands as the SAP particles swell when absorbing fluid, wherein at least some of the SAP particles is extruded out of the network as the absorbing filling material reaches a total absorbent capacity.

8. The generally planar absorbent member according to claim 7 in which the upper cover comprises a porous fabric and the lower cover comprising a flexible film adapted to transmit fluid or urine flow from the interior cavity and block fluid or urine flow into the interior cavity.

9. The generally planar absorbent member according to claim 7 wherein the lower cover has an exterior surface facing away from the upper cover, the exterior surface being having one or more portion with an adhesive material for attachment to non-woven fabric of a diaper.

10. An absorbent garment comprising:
an interior surface configured with a fluid porous inner surface that is configured to face a wearer,
a fluid impervious outer surface opposing the inner surface and configured to face outward from the wearer,
a fluid absorbent core disposed between that has a plurality of layers in which at least some of the layers consist essentially of super absorbent polymer (SAP) particles dispersed in a network of non-hydrophilic fibers,
wherein the network of non-hydrophilic fibers expands as the SAP particles swell when absorbing fluid, wherein at least some of the SAP particles is extruded out of the network as the absorbing filling material reaches a total absorbent capacity.

11. The absorbent garment according to claim 10 wherein at least one of the layers in the plurality has a mixture of different SAP particles, in which some of the SAP particles have a different rate of fluid absorption that the other SAP particles in the mixture.

12. The absorbent garment according to claim 10 wherein the interior surface is a 3D non woven fabric.

* * * * *